(12) United States Patent
Tokarski et al.

(10) Patent No.: US 7,108,948 B2
(45) Date of Patent: *Sep. 19, 2006

(54) ORGANOPHOTORECEPTOR WITH CHARGE TRANSPORT COMPOSITIONS

(75) Inventors: Zbigniew Tokarski, Woodbury, MN (US); Nusrallah Jubran, St. Paul, MN (US); Vytautas Getautis, Kaunas (LT); Juozas V. Grazulevicius, Kaunas (LT); Tadas Malinauskas, Kaunas (LT); Edmundas Montrimas, Vilnius (LT); Valentas Gaidelis, Vilnius (LT)

(73) Assignee: Samsung Electronics Co., LTD, Kyungki-Do (CN)

( * ) Notice: Subject to any disclaimer, the term of this patent is extended or adjusted under 35 U.S.C. 154(b) by 223 days.

This patent is subject to a terminal disclaimer.

(21) Appl. No.: 10/789,077

(22) Filed: Feb. 27, 2004

(65) Prior Publication Data

US 2005/0191570 A1    Sep. 1, 2005

(51) Int. Cl.
G03G 5/04    (2006.01)

(52) U.S. Cl. .................. 430/58.45; 430/74; 430/77; 399/159; 548/135; 564/251

(58) Field of Classification Search ............ 430/58.45, 430/74, 77; 548/135; 564/251; 399/159
See application file for complete search history.

(56) References Cited

U.S. PATENT DOCUMENTS

| | | | |
|---|---|---|---|
| 4,297,426 A | 10/1981 | Sakai et al. | |
| 4,786,571 A | 11/1988 | Ueda | |
| 5,942,615 A | 8/1999 | Kobayashi et al. | |
| 6,066,426 A | 5/2000 | Mott et al. | |
| 6,083,651 A | 7/2000 | Kobayashi et al. | |
| 6,140,004 A | 10/2000 | Mott et al. | |
| 6,214,503 B1 | 4/2001 | Gaidelis et al. | |
| 6,340,548 B1 | 1/2002 | Jubran et al. | |
| 6,670,085 B1 | 12/2003 | Jubran et al. | |
| 6,689,523 B1 | 2/2004 | Law et al. | |
| 6,696,209 B1 | 2/2004 | Law et al. | |
| 6,815,133 B1 * | 11/2004 | Law et al. | 430/58.45 |
| 2003/0104294 A1 | 6/2003 | Law et al. | |
| 2003/0113132 A1 | 6/2003 | Law et al. | |
| 2003/0113643 A1 | 6/2003 | Law et al. | |
| 2003/0113644 A1 | 6/2003 | Law et al. | |
| 2003/0129513 A1 | 7/2003 | Jubran et al. | |
| 2003/0138712 A1 | 7/2003 | Law et al. | |
| 2003/0198880 A1 | 10/2003 | Law et al. | |
| 2003/0203296 A1 | 10/2003 | Law et al. | |
| 2003/0219662 A1 | 11/2003 | Jubran et al. | |

FOREIGN PATENT DOCUMENTS

| | | |
|---|---|---|
| DE | 816923 | 7/1959 |
| DE | 3147118 | 7/1982 |
| EP | 1202120 | 5/2002 |
| EP | 1310489 | 10/2002 |
| EP | 1550914 | 11/2004 |
| JP | 2001-166519 | 6/2001 |

OTHER PUBLICATIONS

M. Daskeviciene et al., "Derivatives of 2,5-Dimercapto-1,3,4-thiazole as Hole Transporting Materials," Lithuanian Journal of Physics, 2001, 41, No. 4-6, 521-526.

S.R.Jain et al, "Novel Energetic N-N Bonded Polymeric Binders for Composite Propellants," Macromolecules New Frontiers, p. 1018-1021, Allied Publishers Ltd., New Delhi, 1998.

P.M. Thangamathesvaran and S.R. Jain, "Synthesis, Characterization And Binding Properties Of Epoxy Resins Based On Carbonohydrazones And Thiocarbonohydrazones," *Frontiers of Polymer Research*, p. 589-594, Edited by P.N. Prasad and J.K. Nigam, Plenum Press, NY, 1991.

* cited by examiner

*Primary Examiner*—John L Goodrow
(74) *Attorney, Agent, or Firm*—Patterson, Thuente, Skaar & Christensen, P.A.

(57) ABSTRACT

An organophotoreceptor comprises an electrically conductive substrate and photoconductive element on the electrically conductive substrate, the photoconductive element having
a) a charge transport composition with the formula $$*{-}[X_1 \quad X_2]_n{-}* $$
$$R_1 \diagdown_{\phantom{N}} \diagup R_2$$
$$\phantom{R_1}N{-}N{-}Z{-}N{-}N\phantom{R_2}$$
$$Y_1 \diagup \phantom{NNZNN} \diagdown Y_2$$

where $Y_1$ and $Y_2$ are, each independently, an arylamine group;
$X_1$ and $X_2$ are, each independently, a linking group;
$R_1$ and $R_2$ are, each independently, a hydrogen, an alkyl group, an alkenyl group, a heterocyclic group, an aromatic group;
Z is a bridging group; and
n is a distribution of integers between 1 and 100,000 with an average value greater than 1; and
(b) a charge generating compound.

Corresponding electrophotographic apparatuses and imaging methods are described.

40 Claims, No Drawings

ORGANOPHOTORECEPTOR WITH CHARGE TRANSPORT COMPOSITIONS

FIELD OF THE INVENTION

This invention relates to organophotoreceptors suitable for use in electrophotography and, more specifically, to organophotoreceptors having a charge transport composition or a polymeric charge transport material comprising a polymer having repeating units comprising two hydrazone groups bonded together through a bridging group.

BACKGROUND OF THE INVENTION

In electrophotography, an organophotoreceptor in the form of a plate, disk, sheet, belt, drum or the like having an electrically insulating photoconductive element on an electrically conductive substrate is imaged by first uniformly electrostatically charging the surface of the photoconductive layer, and then exposing the charged surface to a pattern of light. The light exposure selectively dissipates the charge in the illuminated areas where light strikes the surface, thereby forming a pattern of charged and uncharged areas, referred to as a latent image. A liquid or dry toner is then provided in the vicinity of the latent image, and toner droplets or particles deposit in the vicinity of either the charged or uncharged areas to create a toned image on the surface of the photoconductive layer. The resulting toned image can be transferred to a suitable ultimate or intermediate receiving surface, such as paper, or the photoconductive layer can operate as an ultimate receptor for the image. The imaging process can be repeated many times to complete a single image, for example, by overlaying images of distinct color components or effect shadow images, such as overlaying images of distinct colors to form a full color final image, and/or to reproduce additional images.

Both single layer and multilayer photoconductive elements have been used. In single layer embodiments, a charge transport composition and charge generating material are combined with a polymeric binder and then deposited on the electrically conductive substrate. In multilayer embodiments, the charge transport material and charge generating material are present in the element in separate layers, each of which can optionally be combined with a polymeric binder, deposited on the electrically conductive substrate. Two arrangements are possible for a two-layer photoconductive element. In one two-layer arrangement (the "dual layer" arrangement), the charge-generating layer is deposited on the electrically conductive substrate and the charge transport layer is deposited on top of the charge generating layer. In an alternate two-layer arrangement (the "inverted dual layer" arrangement), the order of the charge transport layer and charge generating layer is reversed.

In both the single and multilayer photoconductive elements, the purpose of the charge generating material is to generate charge carriers (i.e., holes and/or electrons) upon exposure to light. The purpose of the charge transport material is to accept at least one type of these charge carriers and transport them through the charge transport layer in order to facilitate discharge of a surface charge on the photoconductive element. The charge transport material can be a charge transport compound, an electron transport compound, or a combination of both. When a charge transport compound is used, the charge transport compound accepts the hole carriers and transports them through the layer with the charge transport compound. When an electron transport compound is used, the electron transport compound accepts the electron carriers and transports them through the layer with the electron transport compound.

Organophotoreceptors may be used for both dry and liquid electrophotography. There are many differences between dry and liquid electrophotography. A significant difference is that a dry toner is used in dry electrophotography, whereas a liquid toner is used in liquid electrophotography. A potential advantage of liquid electrophotography is that it can provide a higher resolution and thus sharper images than dry electrophotography because liquid toner particles can be generally significantly smaller than dry toner particles. As a result of their smaller size, liquid toners are able to provide images of higher optical density than dry toners.

In both dry and liquid electrophotography, the charge transport material used for the organophotoreceptor should be compatible with the polymeric binder in the photoconductive element. The selection of a suitable polymeric binder for a particular charge transport material can place constraints on the formation of the photoconductive element. If the charge transport material is not compatible with the polymeric binder, the charge transport material may phase-separate or crystallize in the polymeric binder matrix, or may diffuse onto the surface of the layer containing the charge transport material. If such incompatibility occurs, the organophotoreceptor can cease to transport charges.

Furthermore, liquid electrophotography faces an additional issue. In particular, the organophotoreceptor for liquid electrophotography is in contact with the liquid carrier of a liquid toner while the toner dries or pending transfer to a receiving surface. As a result, the charge transport material in the photoconductive element may be removed by extraction by the liquid carrier. Over a long period of operation, the amount of the charge transport material removed by extraction may be significant and, therefore, detrimental to the performance of the organophotoreceptor.

SUMMARY OF THE INVENTION

This invention provides organophotoreceptors having good electrostatic properties such as high $V_{acc}$ and low $V_{dis}$. This invention also provides polymeric charge transport compositions having reduced extraction by liquid carriers and reducing the need for a polymeric binder.

In a first aspect, an organophotoreceptor comprises an electrically conductive substrate and a photoconductive element on the electrically conductive substrate, the photoconductive element comprising a) a charge transport composition having the formula:

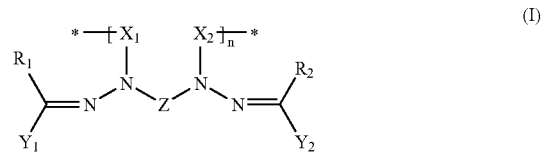

where $Y_1$ and $Y_2$ are, each independently, an arylamine group;

$X_1$ and $X_2$ are, each independently, a linking group, such as a $-(CH_2)_m-$ group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R^d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

$R_1$ and $R_2$ are, each independently, a hydrogen, an alkyl group, an alkenyl group, a heterocyclic group, an aromatic group;

Z is a bridging group, such as a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group; and n is a distribution of integers between 1 and 100,000 with an average value of greater than one; and (b) a charge generating compound.

The asterisks (*) indicate terminal groups on the polymer, which may vary between different polymer units depending on the state of the particular polymerization process at the end of the polymerization step.

The organophotoreceptor may be provided in the form of a plate, a flexible belt, a flexible disk, a sheet, a rigid drum, or a sheet around a rigid or compliant drum. In one embodiment, the organophotoreceptor includes: (a) a photoconductive element comprising the charge transport composition, the charge generating compound, a second charge transport material, and a polymeric binder; and (b) the electrically conductive substrate.

In a second aspect, the invention features an electrophotographic imaging apparatus that includes (a) a light imaging component; and (b) the above-described organophotoreceptor oriented to receive light from the light imaging component. The apparatus preferably further includes a toner dispenser, such as liquid toner dispenser. The method of electrophotographic imaging with photoreceptors containing these novel charge transport compounds is also described.

In a third aspect, the invention features an electrophotographic imaging process that includes (a) applying an electrical charge to a surface of the above-described organophotoreceptor; (b) imagewise exposing the surface of the organophotoreceptor to radiation to dissipate charge in selected areas and thereby form a pattern of at least relatively charged and uncharged areas on the surface; (c) contacting the surface with a toner, such as a liquid toner that includes a dispersion of colorant particles in an organic liquid, to create a toned image; and (d) transferring the toned image to a substrate.

In a fourth aspect, the invention features desirable charge transport compositions having Formula (I) above.

These photoreceptors can be used successfully with toners, such as liquid and dry toners, to produce high quality images. The high quality of the imaging system is maintained after repeated cycling.

Other features and advantages of the invention will be apparent from the following description of the preferred embodiments thereof, and from the claims.

DETAILED DESCRIPTION OF PREFERRED EMBODIMENTS

An organophotoreceptor as described herein has an electrically conductive substrate and a photoconductive element comprising a charge generating compound and a charge transport composition or a polymeric charge transport material having repeating units comprising two hydrazone groups bonded together through a bridging group. The charge transport composition can have desirable properties for use within organophotoreceptors for electrophotography. In particular, the charge transport composition of this invention can have low solubility in carrier liquid and good compatibility with various binder materials, can be incorporated in both the single and multilayer photoconductive elements, and can possess excellent electrophotographic properties. The organophotoreceptors according to this invention generally can have a high photosensitivity, a low residual potential, and a high stability with respect to cycle testing, crystallization, and organophotoreceptor bending and stretching. The organophotoreceptors are particularly useful in laser printers and the like as well as photocopiers, scanners and other electronic devices based on electrophotography. The use of these polymeric charge transport materials is described in more detail below in the context of laser printer use, although their application in other devices operating by electrophotography can be generalized from the discussion below.

To produce high quality images, particularly after multiple cycles, it is desirable for the charge transport materials to form a homogeneous solution with the polymeric binder and remain approximately homogeneously distributed through the organophotoreceptor material during the cycling of the material. In addition, it is desirable to increase the amount of charge that the charge transport material can accept (indicated by a parameter known as the acceptance voltage or "$V_{acc}$"), and to reduce retention of that charge upon discharge (indicated by a parameter known as the discharge voltage or "$V_{dis}$").

The charge transport materials can be classified as charge transport compound or electron transport compound. There are many charge transport compounds and electron transport compounds known in the art for electrophotography. Non-limiting examples of charge transport compounds include, for example, pyrazoline derivatives, fluorene derivatives, oxadiazole derivatives, stilbene derivatives, enamine derivatives, enamine stilbene derivatives, hydrazone derivatives, carbazole hydrazone derivatives, triaryl amines, polyvinyl carbazole, polyvinyl pyrene, polyacenaphthylene, or multi-hydrazone compounds comprising at least two hydrazone groups and at least two groups selected from the group consisting of arylamines such as (N,N-disubstituted)arylamines and heterocycles such as carbazole, julolidine, phenothiazine, phenazine, phenoxazine, phenoxathiin, thiazole, oxazole, isoxazole, dibenzo(1,4)dioxine, thianthrene, imidazole, benzothiazole, benzotriazole, benzoxazole, benzimidazole, quinoline, isoquinoline, quinoxaline, indole, indazole, pyrrole, purine, pyridine, pyridazine, pyrimidine, pyrazine, triazole, oxadiazole, tetrazole, thiadiazole, benzisoxazole, benzisothiazole, dibenzofuran, dibenzothiophene, thiophene, thianaphthene, quinazoline, or cinnoline.

Generally, an electron transport compound has an electron affinity that is large relative to potential electron traps while yielding an appropriate electron mobility in a composite with a polymer. In some embodiments, the electron transport compound has a reduction potential less than $O_2$. In general, electron transport compounds are easy to reduce and difficult to oxidize while charge transport compounds generally are easy to oxidize and difficult to reduce. In some embodiments, the electron transport compounds have a room temperature, zero field electron mobility of at least about $1 \times 10^{-13}$ cm$^2$/Vs, in further embodiments at least about $1 \times 10^{-10}$ cm$^2$/Vs, in additional embodiments at least about $1 \times 10^{-8}$ cm$^2$/Vs, and in other embodiments at least about $1 \times 10^{-6}$ cm$^2$/Vs. A person of ordinary skill in the art will recognize that other ranges of electron mobility within the explicit ranges are contemplated and are within the present disclosure.

Non-limiting examples of electron transport compounds include, for example, bromoaniline, tetracyanoethylene, tetracyanoquinodimethane, 2,4,7-trinitro-9-fluorenone, 2,4,5,7-tetranitro-9-fluorenone, 2,4,5,7-tetranitroxanthone, 2,4,8-trinitrothioxanthone, 2,6,8-trinitro-indeno4H-indeno[1,2-b]thiophene-4-one, and 1,3,7-trinitrodibenzo thiophene-5,5-dioxide, (2,3-diphenyl-1-indenylidene)malononitrile, 4H-thiopyran-1,1-dioxide and its derivatives such as 4-dicyanomethylene-2,6-diphenyl-4H-thiopyran-1,1-dioxide, 4-dicyanomethylene-2,6-di-m-tolyl-4H-thiopyran-1,1-dioxide, and unsymmetrically substituted 2,6-diaryl-4H-thiopyran-1,1-dioxide such as 4H-1,1-dioxo-2-(p-isopropylphenyl)-6-phenyl-4-(dicyanomethylidene)thiopyran and 4H-1,1-dioxo-2-(p-isopropylphenyl)-6-(2-thienyl)-4-(dicyanomethylidene)thiopyran, derivatives of phospha-2,5-cyclohexadiene, alkoxycarbonyl-9-fluorenylidene)malononitrile derivatives such as (4-n-butoxycarbonyl-9-fluorenylidene)malononitrile, (4-phenethoxycarbonyl-9-fluorenylidene)malononitrile, (4-carbitoxy-9-fluorenylidene)malononitrile, and diethyl(4-n-butoxycarbonyl-2,7-dinitro-9-fluorenylidene)malonate, anthraquinodimethane derivatives such as 11,11,12,12-tetracyano-2-alkylanthraquinodimethane and 11,11-dicyano-12,12-bis(ethoxycarbonyl)anthraquinodimethane, anthrone derivatives such as 1-chloro-10-[bis(ethoxycarbonyl)methylene]anthrone, 1,8-dichloro-10-[bis(ethoxy carbonyl)methylene]anthrone, 1,8-dihydroxy-10-[bis(ethoxycarbonyl)methylene]anthrone, and 1-cyano-10-[bis(ethoxycarbonyl)methylene]anthrone, 7-nitro-2-aza-9-fluoroenylidenemalononitrile, diphenoquinone derivatives, benzoquinone derivatives, naphthoquinone derivatives, quinine derivatives, tetracyanoethylenecyanoethylene, 2,4,8-trinitrothioxantone, dinitrobenzene derivatives, dinitroanthracene derivatives, dinitroacridine derivatives, nitroanthraquinone derivatives, dinitroanthraquinone derivatives, succinic anhydride, maleic anhydride, dibromomaleic anhydride, pyrene derivatives, carbazole derivatives, hydrazone derivatives, N,N-dialkylaniline derivatives, diphenylamine derivatives, triphenylamine derivatives, triphenylmethane derivatives, tetracyanoquinodimethane, 2,4,5,7-tetranitro-9-fluorenone, 2,4,7-trinitro-9-dicyanomethylenefluorenone, 2,4,5,7-tetranitroxanthone derivatives, 2,4,8-trinitrothioxanthone derivatives, 1,4,5,8-naphthalene bis-dicarboximide derivatives as described in U.S. Pat. Nos. 5,232,800, 4,468,444, and 4,442,193 and phenylazoquinolide derivatives as described in U.S. Pat. No. 6,472,514. In some embodiments of interest, the electron transport compound comprises an (alkoxycarbonyl-9-fluorenylidene)malononitrile derivative, such as (4-n-butoxycarbonyl-9-fluorenylidene)malononitrile, and 1,4,5,8-naphthalene bis-dicarboximide derivatives.

Although there are many charge transport materials available, there is a need for other charge transport materials to meet the various requirements of particular electrophotography applications. Polymeric charge transport materials have the potential advantage of being less physically mobile within a polymer binder. In particular, if the polymeric charge transport material is compatible with the polymer binder, the polymers can entangle with each other such that the polymeric charge transport material is much less susceptible to extraction by a liquid carrier associated with a liquid toner or the like.

In electrophotography applications, a charge-generating compound within an organophotoreceptor absorbs light to form electron-hole pairs. These electrons and holes can be transported over an appropriate time frame under a large electric field to discharge locally a surface charge that is generating the field. The discharge of the field at a particular location results in a surface charge pattern that essentially matches the pattern drawn with the light. This charge pattern then can be used to guide toner deposition. The polymeric charge transport materials described herein can be effective at transporting charge, holes and/or electrons, from the electron-hole pairs formed by the charge generating compound. In some embodiments, a specific electron transport compound or charge transport compound can also be used along with the polymeric charge transport material of this invention.

The layer or layers of materials containing the charge generating compound and the charge transport materials are within an organophotoreceptor. To print a two dimensional image using the organophotoreceptor, the organophotoreceptor has a two dimensional surface for forming at least a portion of the image. The imaging process then continues by cycling the organophotoreceptor to complete the formation of the entire image and/or for the processing of subsequent images.

The organophotoreceptor may be provided in the form of a plate, a flexible belt, a disk, a rigid drum, a sheet around a rigid or compliant drum, or the like. The charge transport material can be in the same layer as the charge generating compound and/or in a different layer from the charge generating compound. Additional layers can be used also, as described further below.

In some embodiments, the organophotoreceptor material comprises, for example: (a) a charge transport layer comprising the polymeric charge transport material and a polymeric binder; (b) a charge generating layer comprising the charge generating compound and a polymeric binder; and (c) the electrically conductive substrate. The charge transport layer may be intermediate between the charge generating layer and the electrically conductive substrate. Alternatively, the charge generating layer may be intermediate between the charge transport layer and the electrically conductive substrate. In further embodiments, the organophotoreceptor material has a single layer with both a charge transport material and a charge generating compound within a polymeric binder.

The organophotoreceptors can be incorporated into an electrophotographic imaging apparatus, such as laser printers. In these devices, an image is formed from physical embodiments and converted to a light image that is scanned onto the organophotoreceptor to form a surface latent image. The surface latent image can be used to attract toner onto the surface of the organophotoreceptor, in which the toner image is the same or the negative of the light image projected onto the organophotoreceptor. The toner can be a liquid toner or a dry toner. The toner is subsequently transferred, from the surface of the organophotoreceptor, to a receiving surface, such as a sheet of paper. After the transfer of the toner, the entire surface is discharged, and the material is ready to cycle again. The imaging apparatus can further comprise, for example, a plurality of support rollers for transporting a paper receiving medium and/or for movement of the photoreceptor, a light imaging component with suitable optics to form the light image, a light source, such as a laser, a toner source and delivery system and an appropriate control system.

An electrophotographic imaging process generally can comprise (a) applying an electrical charge to a surface of the above-described organophotoreceptor; (b) imagewise exposing the surface of the organophotoreceptor to radiation to dissipate charge in selected areas and thereby form a pattern of charged and uncharged areas on the surface; (c) exposing the surface with a toner, such as a liquid toner that includes a dispersion of colorant particles in an organic liquid to create a toner image, to attract toner to the charged or discharged regions of the organophotoreceptor; and (d) transferring the toner image to a substrate.

As described herein, an organophotoreceptor comprises a charge transport composition comprising molecules having the formula

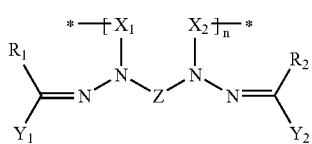

(I)

where $Y_1$ and $Y_2$ are, each independently, an arylamine group;

$X_1$ and $X_2$ are, each independently, a linking group, such as a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

$R_1$ and $R_2$ are, each independently, a hydrogen, an alkyl group, an alkenyl group, a heterocyclic group, an aromatic group;

Z is a bridging group, such as a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group; and n is a distribution of integers between 1 and 100,000 with an average value of greater than one.

The arylamine group includes, but is not limited to, an (N,N-disubstituted)arylamine group (e.g., triarylamine group, alkyldiarylamine group, and dialkylarylamine group), a julolidine group, and a carbazole group.

The heterocyclic group includes any monocyclic or polycyclic (e.g., bicyclic, tricyclic, etc.) ring compound having at least a heteroatom (e.g., O, S, N, P, B, Si, etc.) in the ring.

An aromatic group can be any conjugated ring system containing 4n+2 pi-electrons. There are many criteria available for determining aromaticity. A widely employed criterion for the quantitative assessment of aromaticity is the resonance energy. Specifically, an aromatic group has a resonance energy. In some embodiments, the resonance energy of the aromatic group is at least 10 KJ/mol. In further embodiments, the resonance energy of the aromatic group is greater than 0.1 KJ/mol. Aromatic groups may be classified as an aromatic heterocyclic group which contains at least a heteroatom in the 4n+2 pi-electron ring, or as an aryl group which does not contain a heteroatom in the 4n+2 pi-electron ring. The aromatic group may comprise a combination of aromatic heterocyclic group and aryl group. Nonetheless, either the aromatic heterocyclic or the aryl group may have at least one heteroatom in a substituent attached to the 4n+2 pi-electron ring. Furthermore, either the aromatic heterocyclic or the aryl group may comprise a monocyclic or polycyclic (such as bicyclic, tricyclic, etc.) ring.

Non-limiting examples of the aromatic heterocyclic group are furanyl, thiophenyl, pyrrolyl, indolyl, carbazolyl, benzofuranyl, benzothiophenyl, dibenzofuranyl, dibenzothiophenyl, pyridinyl, pyridazinyl, pyrimidinyl, pyrazinyl, triazinyl, tetrazinyl, petazinyl, quinolinyl, isoquinolinyl, cinnolinyl, phthalazinyl, quinazolinyl, quinoxalinyl, naphthyridinyl, pteridinyl, acridinyl, phenanthridinyl, phenanthrolinyl, anthyridinyl, purinyl, pteridinyl, alloxazinyl, phenazinyl, phenothiazinyl, phenoxazinyl, phenoxathiinyl, dibenzo(1,4)dioxinyl, thianthrenyl, and a combination thereof. The aromatic heterocyclic group may also include any combination of the above aromatic heterocyclic groups bonded together either by a bond (as in bicarbazolyl) or by a linking group (as in 1,6 di(10H-10-phenothiazinyl)hexane). The linking group may include an aliphatic group, an aromatic group, a heterocyclic group, or a combination thereof. Furthermore, either an aliphatic group or an aromatic group within a linking group may comprise at least one heteroatom such as O, S, Si, and N.

Non-limiting examples of the aryl group are phenyl, naphthyl, benzyl, or tolanyl group, sexiphenylene, phenanthrenyl, anthracenyl, coronenyl, and tolanylphenyl. The aryl group may also include any combination of the above aryl groups bonded together either by a bond (as in biphenyl group) or a linking group (as in stilbenyl, diphenyl sulfone, an arylamine group). The linking group may include an aliphatic group, an aromatic group, a heterocyclic group, or a combination thereof. Furthermore, either an aliphatic group or an aromatic group within a linking group may comprise at least one heteroatom such as O, S, Si, and N.

Substitution is liberally allowed on the chemical groups to affect various physical effects on the properties of the compounds, such as mobility, sensitivity, solubility, stability, and the like, as is known generally in the art. In the description of chemical substituents, there are certain practices common to the art that are reflected in the use of language. The terms groups, central nucleus, and moiety have defined meanings. The term group indicates that the generically recited chemical entity (e.g., alkyl group, phenyl group, aromatic group, heterocyclic ring group, epoxy group, thiiranyl group, and aziridinyl group, etc.) may have any substituent thereon which is consistent with the bond structure of that group. For example, where the term 'alkyl group' is used, that term would not only include unsubstituted linear, branched and cyclic alkyls, such as methyl, ethyl, isopropyl, tert-butyl, cyclohexyl, dodecyl and the like, but also substituents having heteroatom, such as 3-ethoxylpropyl, 4-(N,N-diethylamino)butyl, 3-hydroxypentyl, 2-thiolhexyl, 1,2,3-tribromoopropyl, and the like, and aromatic group, such as phenyl, naphthyl, carbazolyl, pyrrole, and the like. However, as is consistent with such nomenclature, no substitution would be included within the term that would alter the fundamental bond structure of the underlying group. For example, where a phenyl group is recited, substitution such as 2- or 4-aminophenyl, 2- or 4-(N,N-disubstituted)aminophenyl, 2,4-dihydroxyphenyl, 2,4,6-trithiophenyl, 2,4,6-trimethoxyphenyl and the like would be acceptable within the terminology, while substitution of 1,1,2,2,3,3-hexamethylphenyl would not be acceptable as that substitution would require the ring bond structure of the phenyl group to be altered to a non-aromatic form. Similarly, when referring to epoxy group, the compound or substituent cited includes any substitution that does not substantively alter the chemical nature of the epoxy ring in the formula. When referring an (N,N-disubstituted)arylamine group, the two substituents attached to the nitrogen may be any group that will not substantively alter the chemical nature of the amine group. Where the term moiety is used, such as alkyl moiety or phenyl moiety, that terminology indicates that the chemical material is not substituted. Where the term alkyl moiety is used, that term represents only an unsubstituted alkyl hydrocarbon group, whether branched, straight chain, or cyclic.

Organophotoreceptors

The organophotoreceptor may be, for example, in the form of a plate, a sheet, a flexible belt, a disk, a rigid drum, or a sheet around a rigid or compliant drum, with flexible belts and rigid drums generally being used in commercial embodiments. The organophotoreceptor may comprise, for example, an electrically conductive substrate and on the electrically conductive substrate a photoconductive element in the form of one or more layers. The photoconductive element can comprise both a charge transport material and a charge generating compound in a polymeric binder, which may or may not be in the same layer, as well as a second charge transport material such as a charge transport compound or an electron transport compound in some embodiments. For example, the charge transport material and the charge generating compound can be in a single layer. In other embodiments, however, the photoconductive element comprises a bilayer construction featuring a charge generating layer and a separate charge transport layer. The charge generating layer may be located intermediate between the electrically conductive substrate and the charge transport layer. Alternatively, the photoconductive element may have a structure in which the charge transport layer is intermediate between the electrically conductive substrate and the charge generating layer.

The electrically conductive substrate may be flexible, for example in the form of a flexible web or a belt, or inflexible, for example in the form of a drum. A drum can have a hollow cylindrical structure that provides for attachment of the drum to a drive that rotates the drum during the imaging process. Typically, a flexible electrically conductive substrate comprises an electrically insulating substrate and a thin layer of electrically conductive material onto which the photoconductive material is applied.

The electrically insulating substrate may be paper or a film forming polymer such as polyester (e.g., polyethylene terephthalate or polyethylene naphthalate), polyimide, polysulfone, polypropylene, nylon, polyester, polycarbonate, polyvinyl resin, polyvinyl fluoride, polystyrene and the like. Specific examples of polymers for supporting substrates included, for example, polyethersulfone (STABAR™ S-100, available from ICI), polyvinyl fluoride (Tedlar®, available from E.I. DuPont de Nemours & Company), polybisphenol-A polycarbonate (MAKROFOL™, available from Mobay Chemical Company) and amorphous polyethylene terephthalate (MELINAR™, available from ICI Americas, Inc.). The electrically conductive materials may be graphite, dispersed carbon black, iodine, conductive polymers such as polypyrroles and Calgon® conductive polymer 261 (commercially available from Calgon Corporation, Inc., Pittsburgh, Pa.), metals such as aluminum, titanium, chromium, brass, gold, copper, palladium, nickel, or stainless steel, or metal oxide such as tin oxide or indium oxide. In embodiments of particular interest, the electrically conductive material is aluminum. Generally, the photoconductor substrate has a thickness adequate to provide the required mechanical stability. For example, flexible web substrates generally have a thickness from about 0.01 to about 1 mm, while drum substrates generally have a thickness from about 0.5 mm to about 2 mm.

The charge generating compound is a material that is capable of absorbing light to generate charge carriers, such as a dye or pigment. Non-limiting examples of suitable charge generating compounds include, for example, metal-free phthalocyanines (e.g., ELA 8034 metal-free phthalocyanine available from H.W. Sands, Inc. or Sanyo Color Works, Ltd., CGM-X01), metal phthalocyanines such as titanium phthalocyanine, copper phthalocyanine, oxytitanium phthalocyanine (also referred to as titanyl oxyphthalocyanine, and including any crystalline phase or mixtures of crystalline phases that can act as a charge generating compound), hydroxygallium phthalocyanine, squarylium dyes and pigments, hydroxy-substituted squarylium pigments, perylimides, polynuclear quinones available from Allied Chemical Corporation under the trade name INDOFAST™ Double Scarlet, INDOFAST™ Violet Lake B, INDOFAST™ Brilliant Scarlet and INDOFAS™ Orange, quinacridones available from DuPont under the trade name MONASTRAL™ Red, MONASTRAL™ M Violet and MONASTRAL™ Red Y, naphthalene 1,4,5,8-tetracarboxylic acid derived pigments including the perinones, tetrabenzoporphyrins and tetranaphthaloporphyrins, indigo- and thioindigo dyes, benzothioxanthene-derivatives, perylene 3,4,9,10-tetracarboxylic acid derived pigments, polyazo-pigments including bisazo-, trisazo- and tetrakisazo-pigments, polymethine dyes, dyes containing quinazoline groups, tertiary amines, amorphous selenium, selenium alloys such as selenium-tellurium, selenium-tellurium-arsenic and selenium-arsenic, cadmium sulphoselenide, cadmium selenide, cadmium sulphide, and mixtures thereof. For some embodiments, the charge generating compound comprises oxytitanium phthalocyanine (e.g., any phase thereof), hydroxygallium phthalocyanine or a combination thereof.

The photoconductive layer of this invention may optionally contain a second charge transport material which may be a charge transport compound, an electron transport compound, or a combination of both. Generally, any charge transport compound or electron transport compound known in the art can be used as the second charge transport material.

An electron transport compound and a UV light stabilizer can have a synergistic relationship for providing desired electron flow within the photoconductor. The presence of the UV light stabilizers alters the electron transport properties of the electron transport compounds to improve the electron transporting properties of the composite. UV light stabilizers can be ultraviolet light absorbers or ultraviolet light inhibitors that trap free radicals.

UV light absorbers can absorb ultraviolet radiation and dissipate it as heat. UV light inhibitors are thought to trap free radicals generated by the ultraviolet light and after trapping of the free radicals, subsequently to regenerate active stabilizer moieties with energy dissipation. In view of the synergistic relationship of the UV stabilizers with electron transport compounds, the particular advantages of the UV stabilizers may not be their UV stabilizing abilities, although the UV stabilizing ability may be further advantageous in reducing degradation of the organophotoreceptor over time. The improved synergistic performance of organophotoreceptors with layers comprising both an electron transport compound and a UV stabilizer are described further in copending U.S. patent application Ser. No. 10/425,333 filed on Apr. 28, 2003 to Zhu, entitled "Organophotoreceptor With A Light Stabilizer," incorporated herein by reference.

Non-limiting examples of suitable light stabilizer include, for example, hindered trialkylamines such as Tinuvin 144 and Tinuvin 292 (from Ciba Specialty Chemicals, Terrytown, N.Y.), hindered alkoxydialkylamines such as Tinuvin 123 (from Ciba Specialty Chemicals), benzotriazoles such as Tinuvan 328, Tinuvin 900 and Tinuvin 928 (from Ciba Specialty Chemicals), benzophenones such as Sanduvor 3041 (from Clariant Corp., Charlotte, N.C.), nickel compounds such as Arbestab (from Robinson Brothers Ltd, West Midlands, Great Britain), salicylates, cyanocinnamates, benzylidene malonates, benzoates, oxanilides such as Sanduvor VSU (from Clariant Corp., Charlotte, N.C.), triazines such as Cyagard UV-1164 (from Cytec Industries Inc., N.J.), polymeric sterically hindered amines such as Luchem (from Atochem North America, Buffalo, N.Y.). In some embodiments, the light stabilizer is selected from the group consisting of hindered trialkylamines having the following formula:

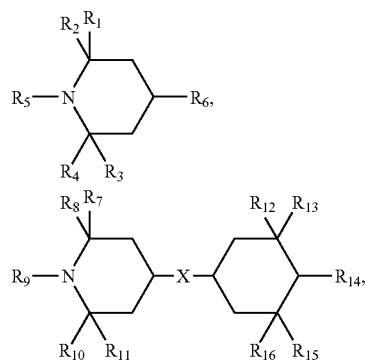

where $R_1$, $R_2$, $R_3$, $R_4$, $R_6$, $R_7$, $R_8$, $R_{10}$, $R_{11}$, $R_{12}$, $R_{13}$, $R_{14}$, $R_{15}$ are, each independently, hydrogen, alkyl group, or ester, or ether group; and $R_5$, $R_9$, and $R_{14}$ are, each independently, alkyl group; and X is a linking group selected from the group consisting of —O—CO—$(CH_2)_m$—CO—O— where m is between 2 to 20.

Optionally, the photoconductive layer may comprise a crosslinking agent linking the charge transport compound and the binder. As is generally true for crosslinking agents in various contexts, the crosslinking agent comprises a plurality of functional groups or at least one functional group with the ability to exhibit multiple functionality. Specifically, a suitable crosslinking agent generally comprises at least one functional group that reacts with an epoxy group and at least one functional group that reacts with a functional group of the polymeric binder. Non-limiting examples of suitable functional groups for reacting with the epoxy group include hydroxyl, thiol, an amino group, carboxyl group, or a combination thereof. In some embodiments, the functional group of the crosslinking agent for reacting with the polymeric binder does not react significantly with the epoxy group. In general, a person of ordinary skill in the art can select the appropriate functional group of the crosslinking agent to react with the polymeric binder, or similarly, a person of ordinary skill in the art can select appropriate functional groups of the polymeric binder to react with the functional group of the crosslinking agent. Suitable functional groups of the crosslinking agent that do not react significantly with the epoxy group, at least under selected conditions, include, for example, epoxy groups, aldehydes and ketones. Suitable reactive binder functional groups for reacting with the aldehydes and ketones include, for example, amines.

In some embodiments, the crosslinking agent is a cyclic acid anhydride, which effectively is at least bifunctional. Non-limiting examples of suitable cyclic acid anhydrides include, for example, 1,8-naphthalene dicarboxylic acid anhydride, itaconic anhydride, glutaric anhydride and citraconic anhydride, fumaric anhydride, phthalic anhydride, isophthalic anhydride, and terephthalic anhydride with maleic anhydride and phthalic anhydride being of particular interest.

The binder generally is capable of dispersing or dissolving the charge transport material (in the case of the charge transport layer or a single layer construction), the charge generating compound (in the case of the charge generating layer or a single layer construction) and/or an electron transport compound for appropriate embodiments. Examples of suitable binders for both the charge generating layer and charge transport layer generally include, for example, polystyrene-co-butadiene, polystyrene-co-acrylonitrile, modified acrylic polymers, polyvinyl acetate, styrene-alkyd resins, soya-alkyl resins, polyvinylchloride, polyvinylidene chloride, polyacrylonitrile, polycarbonates, polyacrylic acid, polyacrylates, polymethacrylates, styrene polymers, polyvinyl butyral, alkyd resins, polyamides, polyurethanes, polyesters, polysulfones, polyethers, polyketones, phenoxy resins, epoxy resins, silicone resins, polysiloxanes, poly(hydroxyether) resins, polyhydroxystyrene resins, novolak, poly(phenylglycidyl ether)-co-dicyclopentadiene, copolymers of monomers used in the above-mentioned polymers, and combinations thereof. Specific suitable binders include, for example, polyvinyl butyral, polycarbonate, and polyester. Non-limiting examples of polyvinyl butyral include BX-1 and BX-5 from Sekisui Chemical Co. Ltd., Japan. Non-limiting examples of suitable polycarbonate include polycarbonate A which is derived from bisphenol-A (e.g. Iupilon-A from Mitsubishi Engineering Plastics, or Lexan 145 from General Electric); polycarbonate Z which is derived from cyclohexylidene bisphenol (e.g. Iupilon-Z from Mitsubishi Engineering Plastics Corp, White Plain, N.Y.); and polycarbonate C which is derived from methylbisphenol A (from Mitsubishi Chemical Corporation). Non-limiting examples of suitable polyester binders include ortho-polyethylene terephthalate (e.g. OPET TR-4 from Kanebo Ltd., Yamaguchi, Japan).

Suitable optional additives for any one or more of the layers include, for example, antioxidants, coupling agents, dispersing agents, curing agents, surfactants, and combinations thereof.

The photoconductive element overall typically has a thickness from about 10 microns to about 45 microns. In the dual layer embodiments having a separate charge generating layer and a separate charge transport layer, charge generation layer generally has a thickness form about 0.5 microns to about 2 microns, and the charge transport layer has a thickness from about 5 microns to about 35 microns. In embodiments in which the charge transport material and the charge generating compound are in the same layer, the layer with the charge generating compound and the charge transport composition generally has a thickness from about 7 microns to about 30 microns. In embodiments with a distinct electron transport layer, the electron transport layer has an average thickness from about 0.5 microns to about 10 microns and in further embodiments from about 1 micron to about 3 microns. In general, an electron transport overcoat layer can increase mechanical abrasion resistance, increases resistance to carrier liquid and atmospheric moisture, and decreases degradation of the photoreceptor by corona gases. A person of ordinary skill in the art will recognize that additional ranges of thickness within the explicit ranges above are contemplated and are within the present disclosure.

Generally, for the organophotoreceptors described herein, the charge generation compound is in an amount from about 0.5 to about 25 weight percent, in further embodiments in an amount from about 1 to about 15 weight percent, and in other embodiments in an amount from about 2 to about 10 weight percent, based on the weight of the photoconductive layer. The charge transport material is in an amount from about 10 to about 80 weight percent, based on the weight of the photoconductive layer, in further embodiments in an amount from about 35 to about 60 weight percent, and in other embodiments from about 45 to about 55 weight percent, based on the weight of the photoconductive layer. The optional second charge transport material, when present, can be in an amount of at least about 2 weight percent, in other embodiments from about 2.5 to about 25 weight percent, based on the weight of the photoconductive layer, and in further embodiments in an amount from about 4 to about 20 weight percent, based on the weight of the photoconductive layer. The binder is in an amount from about 15 to about 80 weight percent, based on the weight of the photoconductive layer, and in further embodiments in an amount from about 20 to about 75 weight percent, based on the weight of the photoconductive layer. A person of ordinary skill in the art will recognize that additional ranges within the explicit ranges of compositions are contemplated and are within the present disclosure.

For the dual layer embodiments with a separate charge generating layer and a charge transport layer, the charge generation layer generally comprises a binder in an amount from about 10 to about 90 weight percent, in further embodiments from about 15 to about 80 weight percent and in some embodiments in an amount from about 20 to about 75 weight percent, based on the weight of the charge generation layer. The optional charge transport material in the charge generating layer, if present, generally can be in an amount of at least about 2.5 weight percent, in further embodiments from about 4 to about 30 weight percent and in other embodiments in an amount from about 10 to about 25 weight percent, based on the weight of the charge generating layer. The charge transport layer generally comprises a binder in an amount from about 20 weight percent to about 70 weight percent and in further embodiments from about 30 weight percent to about 50 weight percent. A person of ordinary skill in the art will recognize that additional ranges of binder concentrations for the dual layer embodiments within the explicit ranges above are contemplated and are within the present disclosure.

For the embodiments with a single layer having a charge generating compound and a charge transport material, the photoconductive layer generally comprises a binder, a charge transport material, and a charge generation compound. The charge generation compound can be in an amount from about 0.05 to about 25 weight percent and in further embodiment in an amount from about 2 to about 15 weight percent, based on the weight of the photoconductive layer. The charge transport material can be in an amount from about 10 to about 80 weight percent, in other embodiments from about 25 to about 65 weight percent, in additional embodiments from about 30 to about 60 weight percent and in further embodiments in an amount from about 35 to about 55 weight percent, based on the weight of the photoconductive layer, with the remainder of the photoconductive layer comprising the binder, and optional additives, such as any conventional additives. A single layer with a charge transport composition and a charge generating compound generally comprises a binder in an amount from about 10 weight percent to about 75 weight percent, in other embodiments from about 20 weight percent to about 60 weight percent, and in further embodiments from about 25 weight percent to about 50 weight percent. Optionally, the layer with the charge generating compound and the charge transport material may comprise a second charge transport material. The optional second charge transport material, if present, generally can be in an amount of at least about 2.5 weight percent, in further embodiments from about 4 to about 30 weight percent and in other embodiments in an amount from about 10 to about 25 weight percent, based on the weight of the photoconductive layer. A person of ordinary skill in the art will recognize that additional composition ranges within the explicit compositions ranges for the layers above are contemplated and are within the present disclosure.

In general, any layer with an electron transport compound can advantageously further include a UV light stabilizer. In particular, the electron transport layer generally can comprise an electron transport compound, a binder, and an optional UV light stabilizer. An overcoat layer comprising an electron transport compound is described further in copending U.S. patent application Ser. No. 10/396,536 to Zhu et al. entitled, "Organophotoreceptor With An Electron Transport Layer," incorporated herein by reference. For example, an electron transport compound as described above may be used in the release layer of the photoconductors described herein. The electron transport compound in an electron transport layer can be in an amount from about 10 to about 50 weight percent, and in other embodiments in an amount from about 20 to about 40 weight percent, based on the weight of the electron transport layer. A person of ordinary skill in the art will recognize that additional ranges of compositions within the explicit ranges are contemplated and are within the present disclosure.

The UV light stabilizer, if present, in any one or more appropriate layers of the photoconductor generally is in an amount from about 0.5 to about 25 weight percent and in some embodiments in an amount from about 1 to about 10 weight percent, based on the weight of the particular layer. A person of ordinary skill in the art will recognize that additional ranges of compositions within the explicit ranges are contemplated and are within the present disclosure.

For example, the photoconductive layer may be formed by dispersing or dissolving the components, such as one or more of a charge generating compound, the polymeric charge transport material of this invention, a second charge transport material such as a charge transport compound or an electron transport compound, a UV light stabilizer, and a polymeric binder in organic solvent, coating the dispersion and/or solution on the respective underlying layer and drying the coating. In particular, the components can be dispersed by high shear homogenization, ball-milling, attritor milling, high energy bead (sand) milling or other size reduction processes or mixing means known in the art for effecting particle size reduction in forming a dispersion.

The photoreceptor may optionally have one or more additional layers as well. An additional layer can be, for example, a sub-layer or an overcoat layer, such as a barrier layer, a release layer, a protective layer, or an adhesive layer. A release layer or a protective layer may form the uppermost layer of the photoconductor element. A barrier layer may be sandwiched between the release layer and the photoconductive element or used to overcoat the photoconductive element. The barrier layer provides protection from abrasion to the underlayers. An adhesive layer locates and improves the adhesion between a photoconductive element, a barrier layer and a release layer, or any combination thereof. A sub-layer is a charge blocking layer and locates between the electrically conductive substrate and the photoconductive element. The sub-layer may also improve the adhesion between the electrically conductive substrate and the photoconductive element.

Suitable barrier layers include, for example, coatings such as crosslinkable siloxanol-colloidal silica coating and hydroxylated silsesquioxane-colloidal silica coating, and organic binders such as polyvinyl alcohol, methyl vinyl ether/maleic anhydride copolymer, casein, polyvinyl pyrrolidone, polyacrylic acid, gelatin, starch, polyurethanes, polyimides, polyesters, polyamides, polyvinyl acetate, polyvinyl chloride, polyvinylidene chloride, polycarbonates, polyvinyl butyral, polyvinyl acetoacetal, polyvinyl formal, polyacrylonitrile, polymethyl methacrylate, polyacrylates, polyvinyl carbazoles, copolymers of monomers used in the above-mentioned polymers, vinyl chloride/vinyl acetate/vinyl alcohol terpolymers, vinyl chloride/vinyl acetate/maleic acid terpolymers, ethylene/vinyl acetate copolymers, vinyl chloride/vinylidene chloride copolymers, cellulose polymers, and mixtures thereof. The above barrier layer polymers optionally may contain small inorganic particles such as fumed silica, silica, titania, alumina, zirconia, or a combination thereof. Barrier layers are described further in U.S. Pat. No. 6,001,522 to Woo et al., entitled "Barrier Layer For Photoconductor Elements Comprising An Organic Polymer And Silica," incorporated herein by reference. The release layer topcoat may comprise any release layer composition known in the art. In some embodiments, the release layer is a fluorinated polymer, siloxane polymer, fluorosilicone polymer, silane, polyethylene, polypropylene, polyacrylate, or a combination thereof. The release layers can comprise crosslinked polymers.

The release layer may comprise, for example, any release layer composition known in the art. In some embodiments, the release layer comprises a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In further embodiments, the release layers comprise crosslinked polymers.

The protective layer can protect the organophotoreceptor from chemical and mechanical degradation. The protective layer may comprise any protective layer composition known in the art. In some embodiments, the protective layer is a fluorinated polymer, siloxane polymer, fluorosilicone polymer, polysilane, polyethylene, polypropylene, polyacrylate, poly(methyl methacrylate-co-methacrylic acid), urethane resins, urethane-epoxy resins, acrylated-urethane resins, urethane-acrylic resins, or a combination thereof. In some embodiments of particular interest, the release layers are crosslinked polymers.

An overcoat layer may comprise an electron transport compound as described further in copending U.S. patent application Ser. No. 10/396,536, filed on Mar. 25, 2003 to Zhu et al. entitled, "Organoreceptor With An Electron Transport Layer," incorporated herein by reference. For example, an electron transport compound, as described above, may be used in the release layer of this invention. The electron transport compound in the overcoat layer can be in an amount from about 2 to about 50 weight percent, and in other embodiments in an amount from about 10 to about 40 weight percent, based on the weight of the release layer. A person of ordinary skill in the art will recognize that additional ranges of composition within the explicit ranges are contemplated and are within the present disclosure.

Generally, adhesive layers comprise a film forming polymer, such as polyester, polyvinylbutyral, polyvinylpyrrolidone, polyurethane, polymethyl methacrylate, poly(hydroxy amino ether) and the like. Barrier and adhesive layers are described further in U.S. Pat. No. 6,180,305 to Ackley et al., entitled "Organic Photoreceptors for Liquid Electrophotography," incorporated herein by reference.

Sub-layers can comprise, for example, polyvinylbutyral, organosilanes, hydrolyzable silanes, epoxy resins, polyesters, polyamides, polyurethanes, cellulosics and the like. In some embodiments, the sub-layer has a dry thickness between about 20 Angstroms and about 20,000 Angstroms. Sublayers containing metal oxide conductive particles can be between about 1 and about 25 microns thick. A person of ordinary skill in the art will recognize that additional ranges of compositions and thickness within the explicit ranges are contemplated and are within the present disclosure.

The polymeric charge transport materials as described herein, and photoreceptors including these compounds, are suitable for use in an imaging process with either dry or liquid toner development. For example, any dry toners and liquid toners known in the art may be used in the process and the apparatus of this invention. Liquid toner development can be desirable because it offers the advantages of providing higher resolution images and requiring lower energy for image fixing compared to dry toners. Examples of suitable liquid toners are known in the art. Liquid toners generally comprise toner particles dispersed in a carrier liquid. The toner particles can comprise a colorant/pigment, a resin binder, and/or a charge director. In some embodiments of liquid toner, a resin to pigment ratio can be from 1:1 to 10:1, and in other embodiments, from 4:1 to 8:1. Liquid toners are described further in Published U.S. Patent Applications 2002/0128349, entitled "Liquid Inks Comprising A Stable Organosol," and 2002/0086916, entitled "Liquid Inks Comprising Treated Colorant Particles," and U.S. Pat. No. 6,649,316, entitled "Phase Change Developer For Liquid Electrophotography," all three of which are incorporated herein by reference.

Charge Transport Composition

The organophotoreceptor described herein comprise a charge transport composition having the formula:

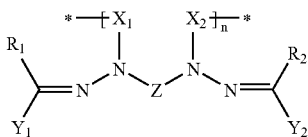

(I)

where $Y_1$ and $Y_2$ are, each independently, an arylamine group;

$X_1$ and $X_2$ are, each independently, a linking group, such as a —$(CH_2)_m$— group, where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

$R_1$ and $R_2$ are, each independently, a hydrogen, an alkyl group, an alkenyl group, a heterocyclic group, an aromatic group;

Z is a bridging group, such as a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group; and n is a distribution of integers between 1 and 100,000 with an average value of greater than one.

In general, the distribution of n values depends on the polymerization conditions. The presence of the polymer of formula (1) does not preclude the presence of unreacted monomer and dimers within the organophotoreceptor, although the concentrations of monomers and dimers would generally be small if not extremely small or undetectable. The extent of polymerization, as specified with n, can affect the properties of the resulting polymer. In some embodiments, an average value of n can be in the hundreds or thousands, although the average value of n may be any value of 3 or greater and in some embodiments any value of 5 or greater and in further embodiments the average value of n is 10 or greater. A person of ordinary skill in the art will recognize that additional ranges of average n values are contemplated and are within the present disclosure.

In some embodiments, the bridging group Z may comprise an alkylene group, an alkenylene group, a heterocyclic group, or an aromatic group. In particular, an aromatic Z group can contribute in desirable ways to the function of the charge transport composition. Non-limiting examples of suitable aromatic groups include the following formulae:

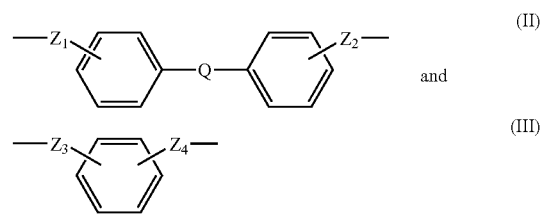

where Q is a bond, O, S, O=S=O, C=O, an aryl group, an $NR_3$ group, or a $CR_4R_5$ group, where $R_3$, $R_4$, and $R_5$ are, each independently, H, an alkyl group, an alkenyl group, a heterocyclic group, an aromatic group, or part of a ring group; and $Z_1$, $Z_2$, $Z_3$, and $Z_4$ are, each independently, a bond or a —$(CH_2)_n$— group where n is an integer between 1 and 20, inclusive, and one or more of the methylene groups is optionally replaced by O, S, N, C, Si, B, P, C=O, O=S=O, a heterocyclic group, an aromatic group, urethane, urea, an ester group, an $NR_6$ group, a $CR_7$ group, a $CR_8R_9$ group, or a $SiR_{10}R_{11}$ group, where $R_6$, $R_7$, $R_8$, $R_9$, $R_{10}$, and $R_{11}$ are, each independently, a bond, H, hydroxyl, thiol, carboxyl, an amino group, an alkyl group, an alkoxy group, an alkenyl group, a heterocyclic group, an aromatic group, or part of a ring group.

In some embodiments, the bridging group Z has a structure according to Formula (II) above where Q is a O=S=O group and $Z_1$ and $Z_2$ are, each independently, a bond. In further embodiments, the charge transport composition has the following formula:

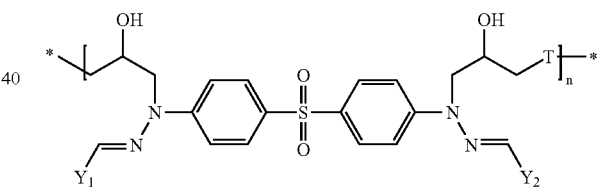

where n is a distribution of integers between 1 and 100,000;

$Y_1$ and $Y_2$ are, each independently, an arylamine group; and

T has one of the following formulae:

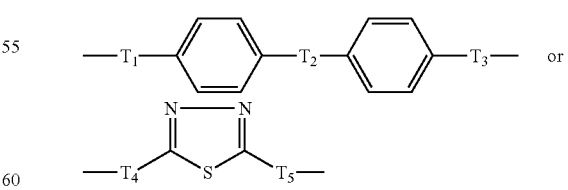

where $T_1$, $T_2$, $T_3$, $T_4$, and $T_5$ are, each independently, O, S, O=S=O, or C=O. Specific, non-limiting examples of suitable charge transport composition within the general Formula (I) of the present invention have the following formulae:

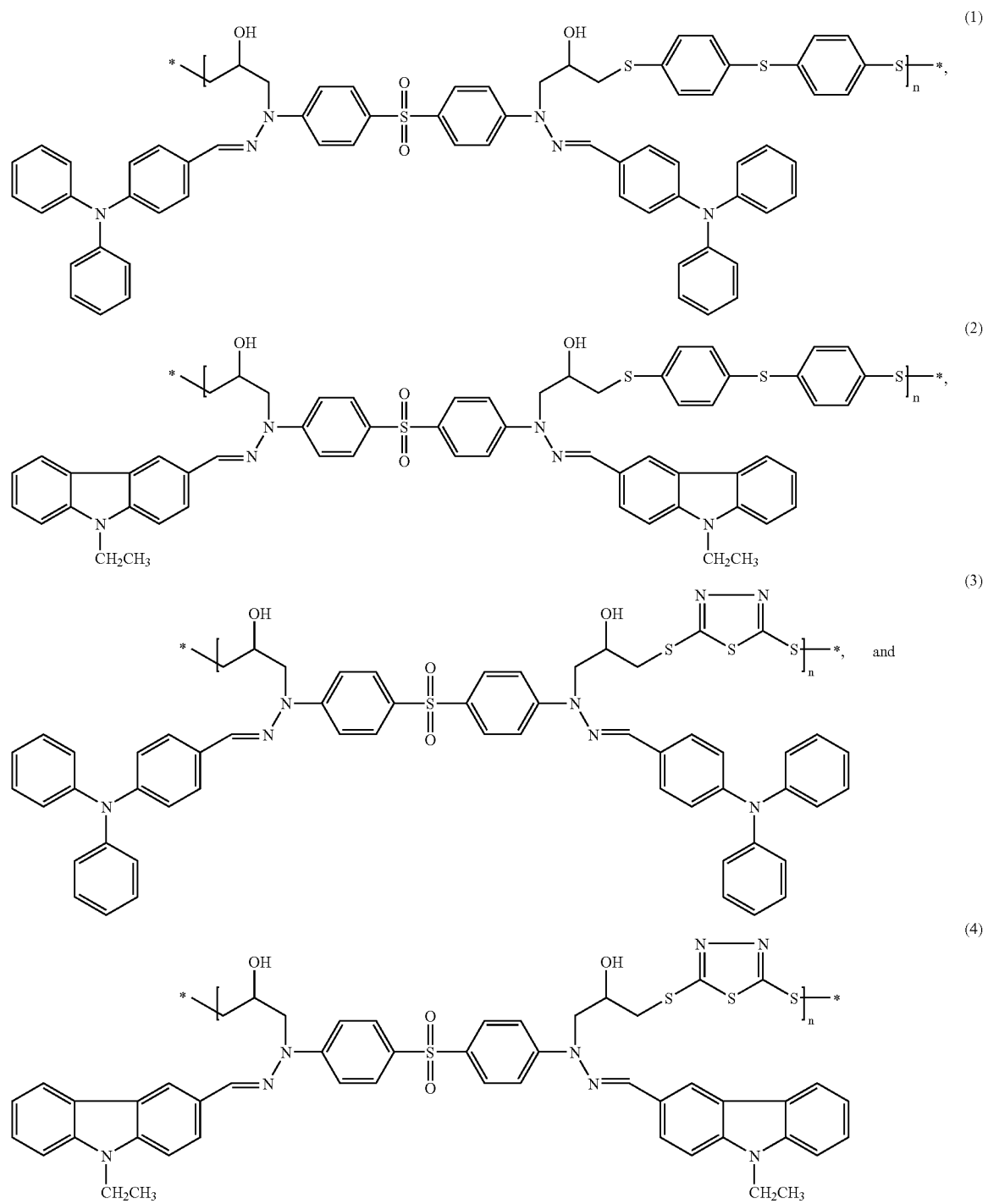

where n is a distribution of integers between 1 and 100,000 with an average value of greater than one and the asterisks (*) indicate terminal groups on the polymer, which may vary between different polymer units depending on the state of the particular polymerization process at the end of the polymerization step.

Synthesis of Charge Transport Compositions

The synthesis of the charge transport compositions of this invention can be prepared by the following multi-step synthetic procedure, although other suitable procedures can be used by a person of ordinary skill in the art based on the disclosure herein.

The charge transport composition of this invention may be prepared by the reaction of a multi-functional compound comprising at least 2 active hydrogens, for example, selected from the group consisting of hydroxyl hydrogen, amino hydrogen, carboxyl hydrogen, and thiol hydrogen with a reactive-ring compound having the following formula

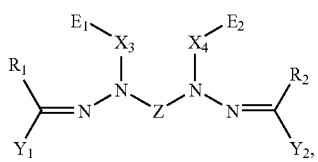

where $Y_1$ and $Y_2$ are, each independently, an arylamine group;

$X_3$ and $X_4$, each independently, comprise a —$(CH_2)_p$— group, where p is an integer between 1 and 20, inclusive, and one or more of the methylene groups is optionally replaced by O, S, N, C, B, Si, P, C=O, O=S=O, a heterocyclic group, an aromatic group, an $NR_m$ group, a $CR_n$ group, a $CR_oR_p$ group, or a $SiR_qR_r$ where $R_m$, $R_n$, $R_o$, $R_p$, $R_q$, and $R_r$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

$R_1$ and $R_2$ are, each independently, a hydrogen, an alkyl group, an alkenyl group, a heterocyclic group, an aromatic group;

Z can comprise a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group; and $E_1$ and $E_2$ are, each independently, a reactive ring group, such as an epoxy ring, a thiiranyl group, an aziridinyl group, and an oxetanyl group.

In some embodiments, the bridging group Z may comprise an alkylene group, an alkenylene group, a heterocyclic group, or an aromatic group. In particular, an aromatic Z group can contribute in desirable ways to the function of the charge transport composition. Non-limiting examples of suitable aromatic groups include the following formulae:

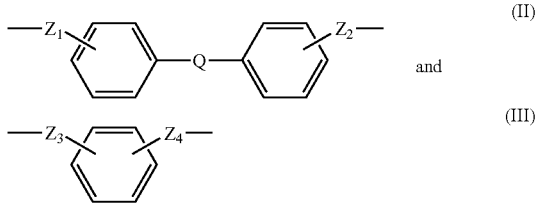

where Q is a bond, O, S, O=S=O, C=O, an aryl group, an $NR_3$ group, or a $CR_4R_5$ group, where $R_3$, $R_4$, and $R_5$ are, each independently, H, an alkyl group, an alkenyl group, a heterocyclic group, an aromatic group, or part of a ring group; and $Z_1$, $Z_2$, $Z_3$, and $Z_4$, each independently, comprise a bond or a —$(CH_2)_n$— group where n is an integer between 1 and 20, inclusive, and one or more of the methylene groups is optionally replaced by O, S, N, C, Si, B, P, C=O, O=S=O, a heterocyclic group, an aromatic group, urethane, urea, an ester group, an $NR_6$ group, a $CR_7$ group, a $CR_8R_9$ group, or a $SiR_{10}R_{11}$ group, where $R_6$, $R_7$, $R_8$, $R_9$, $R_{10}$, and $R_{11}$ are, each independently, a bond, H, hydroxyl, thiol, carboxyl, an amino group, an alkyl group, an alkoxy group, an alkenyl group, a heterocyclic group, an aromatic group, or part of a ring group.

The reactive ring groups, $E_1$ and $E_2$, are selected from the group consisting of heterocyclic ring groups which have a higher strain energy than its corresponding open-ring structure. The conventional definition of strain energy is that it represents the difference in energy between the actual molecule and a completely strain-free molecule of the same constitution. More information about the origin of strain energy can be found in the article by Wiberg et al., "A Theoretical Analysis of Hydrocarbon Properties: II Additivity of Group Properties and the Origin of Strain Energy," J. Am. Chem. Soc. 109, 985 (1987). The above article is incorporated herein by reference. The heterocyclic ring group may have 3, 4, 5, 7, 8, 9, 10, 11, or 12 members, in further embodiments 3, 4, 5, 7, or 8 members, in some embodiment 3, 4, or 8 members, and in additional embodiments 3 or 4 members. Non-limiting examples of such heterocyclic ring are cyclic ethers (e.g., epoxides and oxetane), cyclic amines (e.g., aziridine), cyclic sulfides (e.g., thiirane), cyclic amides (e.g., 2-azetidinone, 2-pyrrolidone, 2-piperidone, caprolactam, enantholactam, and capryllactam), N-carboxy-α-amino acid anhydrides, lactones, and cyclosiloxanes. The chemistry of the above heterocyclic rings is described in George Odian, "Principle of Polymerization," second edition, Chapter 7, p. 508–552 (1981), incorporated herein by reference.

In some embodiments of interest, the reactive ring group is an epoxy group. Some epoxy groups may have the following formula:

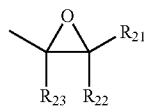

where $R_{21}$, $R_{22}$, and $R_{23}$ are, each independently, hydrogen, an alkyl group, an alkenyl group, or an aromatic group (e.g. phenyl, naphthyl, carbazolyl, stilbenyl), or, when fused together, the atoms necessary to form a 5- or 6-member cycloaliphatic ring.

The di-epoxy-ring compound may be prepared by the following multi-step synthetic procedure, although other suitable procedures can be used by a person of ordinary skill in the art based on the disclosure herein.

The first step is a nucleophilic substitution reaction between a linking organic compound having two halogen groups (i.e. dibromoalkanes or 4,4'-dichlorodiphenyl sulfone) and hydrazine hydrate. The linking organic compound may or may not be symmetric with respect to the two halogen groups. The reaction mixture may be refluxed for 24 hours. The product of the nucleophilic substitution is the corresponding aromatic compound having two hydrazine groups, such as 4,4'-dihydrazinodiphenyl sulfone.

In the second step, the aromatic compound having two hydrazine groups may react with an arylamine having an aldehyde or a keto group to form the corresponding aromatic compound having two hydrazone groups. If desired, two different arylamine compounds can be reacted with the di-hydrazine compound. The use of one or two arylamine reactants with keto groups result in a charge transport material with $R_1$ and/or $R_2$ groups that differ from H. While the use of two different arylamine compounds may result in a mixture of products, a person of ordinary skill in the art can reduce the synthesis of undesired forms of product through either sequential or simultaneous reactions, and the different product compounds can be separated from each other through appropriate purification approaches.

In the third step, the two NH groups of the aromatic compound having two hydrazone groups may react with an organic halide comprising an epoxy group in the presence of an alkaline to form a charge transport material having two epoxidated-hydrazone groups bonded together through a linking group. Non-limiting examples of suitable organic halide comprising an epoxy group for this invention are epihalohydrins, such as epichlorohydrin. The organic halide comprising an epoxy group may also be prepared by the epoxidation reaction of the corresponding organic halide having an olefin group. The epoxidation reaction is described in Carey et al., "Advanced Organic Chemistry, Part B: Reactions and Synthesis," New York, 1983, pp. 494–498, incorporated herein by reference. The organic halide having an olefin group may be prepared by the Wittig reaction between a suitable organic halide having an aldehyde or keto group and a suitable Wittig reagent. The Wittig and related reactions are described in Carey et al., "Advanced Organic Chemistry, Part B: Reactions and Synthesis," New York, 1983, pp. 69–77, incorporated herein by reference. Depending on the particular reactivities of the groups, the order of some of the reactions may be changed.

In some embodiments of interest, the E group is a thiiranyl group. An epoxy compound, such as those described above, can be converted into the corresponding thiiranyl compound by refluxing the epoxy compound and ammonium thiocyanate in tetrahydrofuran. Alternatively, the corresponding thiiranyl compound may be obtained by passing a solution of the above-described epoxy compound through 3-(thiocyano)propyl-functionalized silica gel (commercially available form Aldrich, Milwaukee, Wis.). Alternatively, a thiiranyl compound may be obtained by the thia-Payne rearrangement of a corresponding epoxy compound. The thia-Payne rearrangement is described in Rayner, C. M. Synlett 1997, 11; Liu, Q. Y.; Marchington, A. P.; Rayner, C. M. Tetrahedron 1997, 53, 15729; Ibuka, T. Chem. Soc. Rev. 1998, 27, 145; and Rayner, C. M. Contemporary Organic Synthesis 1996, 3, 499. All the above four articles are incorporated herein by reference. For these embodiments, X' groups can be formed, for example, using a bifunctional group with a halogen and with a thiiranyl group. The halide group can be replaced by a bond to the secondary amine group of the hydrazone by a nucleophilic substitution.

In some embodiments of interest, the E group is an aziridinyl group. An aziridine compound may be obtained by the aza-Payne rearrangement of a corresponding epoxy compound, such as one of those epoxy compounds described above. The thia-Payne rearrangement is described in Rayner, C. M. Synlett 1997, 11; Liu, Q. Y.; Marchington, A. P.; Rayner, C. M. Tetrahedron 1997, 53, 15729; and Ibuka, T. Chem. Soc. Rev. 1998, 27, 145. All the above three articles are incorporated herein by reference. Alternatively, an aziridine compound may be prepared by the addition reaction between a suitable nitrene compound and a suitable alkene. Such addition reaction is described in Carey et al., "Advanced Organic Chemistry, Part B: Reactions and Synthesis," New York, 1983, pp. 446–448, incorporated herein by reference. For these embodiments, X' groups can be formed, for example, using a bifunctional group with a halogen and with an aziridinyl group. The halide group can be replaced by a bond to the secondary amine group of the hydrazone by a nucleophilic substitution.

In some embodiments of interest, the E group is an oxetanyl group. An oxetane compound may be prepared by the Paterno-Buchi reaction between a suitable carbonyl compound and a suitable alkene. The Paterno-Buchi reaction is described in Carey et al., "Advanced Organic Chemistry, Part B: Reactions and Synthesis," New York, 1983, pp. 335–336, incorporated herein by reference. For these embodiment, X' groups can be formed, for example, using a bifunctional group with a halogen and with an oxetanyl group. The halide group can be replaced by a bond to the secondary amine group of the hydrazone by a nucleophilic substitution.

For reaction with the reactive ring groups, the multi-functional compounds, such as di-functional compounds, tri-functional compounds, and tetra-functional compounds, may have two or more active hydrogen atoms, such as hydroxyl hydrogen, thiol hydrogen, amino hydrogen, and carboxyl hydrogen. The active hydrogen atoms in any of the multi-functional compounds may be the same or different. Non-limiting examples of tetra-functional compounds include tetra-hydroxyl compounds, tetra-thiol compounds, tetra-amino compounds, and tetra-carboxylic acids. Non-limiting examples of tri-functional compounds include tri-hydroxyl compounds, tri-thiol compounds, tri-amino compounds, and tri-carboxylic acids. The di-functional compound may be ammonia, a primary amine, a diol, a dithiol, a diamine, a dicarboxlyic acid, a hydroxylamine, an amino acid, a hydroxyl acid, a thiol acid, a hydroxythiol, or a thioamine. Non-limiting examples of suitable dithiol are 4,4'-thiobisbenzenethiol, 1,4-benzenedithiol, 1,3-benzenedithiol, sulfonyl-bis(benzenethiol), 2,5-dimecapto-1,3,4-thiadiazole, 1,2-ethanedithiol, 1,3-propanedithiol, 1,4-butanedithiol, 1,5-pentanedithiol, and 1,6-hexanedithiol. Non-limiting examples of suitable diols are 2,2'-bi-7-naphtol, 1,4-dihydroxybenzene, 1,3-dihydroxybenzene, 10,10-bis(4-hydroxyphenyl)anthrone, 4,4'-sulfonyldiphenol, bisphenol, 4,4'-(9-fluorenylidene)diphenol, 1,10-decanediol, 1,5-pentanediol, diethylene glycol, 4,4'-(9-fluorenylidene)-bis(2-phenoxyethanol), bis(2-hydroxyethyl)terephthalate, bis[4-(2-hydroxyethoxy)phenyl]sulfone, hydroquinone-bis(2-hydroxyethyl)ether, and bis(2-hydroxyethyl)piperazine. Non-limiting examples of suitable diamine are diaminoarenes, and diaminoalkanes. Non-limiting examples of suitable dicarboxylic acid are phthalic acid, terephthalic acid, adipic acid, and 4,4'-biphenyldicarboxylic acid. Non-limiting examples of suitable hydroxylamine are p-aminophenol and fluoresceinamine. Non-limiting examples of suitable amino acid are 4-aminobutyric acid, phenylalanine, and 4-aminobenzoic acid. Non-limiting examples of suitable hydroxyl acid are salicylic acid, 4-hydroxybutyric acid, and 4-hydroxybenzoic acid. Non-limiting examples of suitable hydroxythiol are monothiohydroquinone and 4-mercapto-1-butanol. Non-limiting example of suitable thioamine is p-aminobenzenethiol. Non-limiting example of suitable thiol acid are 4-mercaptobenzoic acid and 4-mercaptobutyric acid. Almost all of the above di-functional compounds are available commercially from Aldrich Chemical Co. and other chemical suppliers.

In some embodiments, the di-functional compound may comprise two functional groups attached to an alkylene group, an alkenylene group, a heterocyclic group, or an aromatic group. Non-limiting examples of suitable aromatic group include the groups having the following formulae:

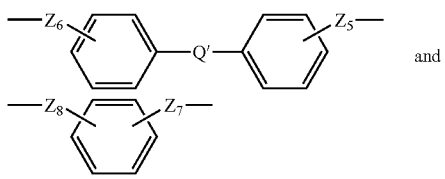

where Q' is a bond, O, S, O=S=O, an $NR_{12}$ group, or a $CR_{13}R_{14}$ group, where $R_{12}$, $R_{13}$, and $R_{14}$ are, each independently, H, an alkyl group, an alkenyl group, a heterocyclic group, an aromatic group, or part of a ring group; and $Z_5$, $Z_6$, $Z_7$, and $Z_8$ are, each independently, a bond or a —$(CH_2)_q$— group where q is an integer between 1 and 20, inclusive, and one or more of the methylene groups is optionally replaced by O, S, N, C, Si, B, P, C=O, O=S=O, a heterocyclic group, an aromatic group, urethane, urea, an ester group, an $NR_{15}$ group, a $CR_{16}$ group, a $CR_{17}R_{18}$ group, or a $SiR_{19}R_{20}$ group, where $R_{15}$, $R_{16}$, $R_{17}$, $R_{18}$, $R_{19}$, and $R_{20}$ are, each independently, a bond, H, hydroxyl, thiol, carboxyl, an amino group, an alkyl group, an alkoxy group, an alkenyl group, a heterocyclic group, an aromatic group, or part of a ring group.

Chemical bonding between the reactive-ring compound and the di-functional compound may be promoted by using a crossing linking agent or an elevated reaction temperature. The reaction temperature may be from 20° C. to 200° C. Preferably, the reaction temperature is between 30° C. to 100° C.

Any conventional crosslinking agent for the reaction between a reactive ring groups, such as epoxy group, and a functional group, such as hydroxyl, thiol, carboxyl, and an amino group, known in the art may be used for this invention. Non-limiting examples of suitable crosslinking agent include acid anhydrides and primary or secondary amines. Non-limiting examples of suitable acid anhydride include 1,8-naphthalene dicarboxylic acid anhydride, itaconic anhydride, glutaric anhydride and citraconic anhydride, fumaric anhydride, phthalic anhydride, isophthalic anhydride, and terephthalic anhydride with maleic anhydride and phthalic anhydride being most preferred. Non-limiting examples of suitable primary or secondary amines include diethylene triamine, triethylene tetramine, m-phenylenediamine.

To synthesize the charge transport compositions, the degree of polymerization, i.e., the average value and/or distribution of n, is determined by the concentrations of the reactants, the reaction conditions and the reaction time. These reaction parameters can be adjusted by a person of ordinary skill in the art, based on the present disclosure, to obtain desired values of the extent of reaction. In general, if a one-to-one ratio is used of the reactive-ring compound and the di-functional compound, the charge transport compositions tends to comprise molecules with both a reactive-ring end group and a functional group. A slight excess of reactive-ring compound tends to result in a greater percentage of the reactive-ring end group. Similarly, a slight excess of the di-functional compound tends to result in a greater percentage of the functional end group.

More specifically, the reactive-ring compound and the di-functional compound react to form small molecules with more than one repeating unit as shown in Formula (I). Under sufficiently dilute reaction conditions and a sufficiently short reaction time, the monomer composition effectively can be formed. To the extent that the reaction proceeds further, small molecules can further react with other monomer units, the reactive-ring compound and/or di-functional compound to form larger molecules that can further react. This reaction process continues until the reaction is stopped. The resulting product generally can be characterized by an average molecular weight and a distribution of molecular weights as well as the amount of each end group. Various techniques used for characterizing polymers generally can be used to characterize correspondingly the polymers described herein.

In general, if a crosslinking agent is used, it may be desirable to react the crosslinking agent first with either the charge transport compound or with the polymer binder before combining the other ingredients. A person of ordinary skill in the art can evaluate the appropriate reaction order, such as combining all of the components at one time or sequentially, for forming the layer with desired properties.

While reactive ring groups provide a versatile synthesis approach for the formation of the polymers described herein, other linking groups Y of Formula (I) above can be formed using other additive reactions that do not involve reactive ring groups. For example, various nucleophilic substitutions can be used. Some non-limiting examples of appropriate reactions include esterification reactions and amidization reactions. A person of ordinary skill in the art will recognize suitable reactive functional groups for polymerization.

The invention will now be described further by way of the following examples.

EXAMPLES

Example 1

Synthesis and Characterization Charge Transport Compositions

This example described the synthesis and characterization of Compositions 1–4 in which the numbers refer to formula numbers above. The characterization involves both chemical characterization and the electronic characterization of materials formed with the compound.

Composition (1)

A suspension of 4,4'-dichlorodiphenyl sulfone (20 g, 0.069 mol, obtained from Aldrich) in hydrazine hydrate (158 ml, from Aldrich) was refluxed for 24 hours. The mixture was cooled to room temperature and crystals precipitated out. The crystals were filtered off and washed 3 times with water and one time with isopropanol. The yield of the product, 4,4'-dihydrazinodiphenyl sulfone, was 15.75 g (81.8%). The product had a melting point of 193–194° C. The literature procedure for the preparation of 4,4'-dihydrazinodiphenyl sulfone was published in *Khimiya Geterotsiklicheskikh Soedinenii*, 11, p. 1508–1510, 1980 (issued in the Republic of Latvia). The article is incorporated herein by reference.

A mixture of 4-(diphenylamino)benzaldehyde (25 g, 0.09 mol, from Aldrich), 4,4'-dihydrazinodiphenyl sulfone (11.37 g, 0.041 mol) and 80 ml of dioxane was added to a 250 ml round bottom flask equipped with a reflux condenser and a magnetic stirrer. The reaction mixture was heated at 50° C. for 2 hours with stirring. The solvent was removed by evaporation to form 4,4'-dihydrazondiphenyl sulfone triphenylaminohydrazone. The yield was 30.1 g (93.4%).

A mixture of 4,4'-dihydrazondiphenyl sulfone triphenylaminohydrazone (30.1 g, 0.038 mol) and epichlorohydrin (68 ml, 0.855 mol, obtained from Aldrich) was added to a 250 ml 3-neck round bottom flask equipped with a reflux condenser, a thermometer and a magnetic stirrer. The reaction mixture was stirred vigorously at 35–40° C. for 7 hours. During this time, powdered 85% potassium hydroxide (KOH, 11.3 g, 0.171 mol) and anhydrous sodium sulfate (Na$_2$SO$_4$, 9 g, 0.0228 mol) were added in three portions with prior cooling of the reaction mixture to 20–25° C. After the termination of the reaction, the mixture was cooled to room temperature and filtered. The organic part was treated with ethyl acetate and washed with distilled water until the pH of the water became neutral. The organic layer was dried over anhydrous magnesium sulfate, treated with activated charcoal, and filtered. The solvents were evaporated to form a di-epoxide. The di-epoxide was purified by column chromatography (silica gel, grade 62, 60–200 mesh, 150 Å, Aldrich) using a mixture of acetone and hexane in a ratio of 1:4 by volume as the eluant. The fractions containing the di-epoxide (the Composition (1) monomer precursor) were collected, and the solvents were evaporated. The di-epoxide was recrystallized from a mixture of acetone and hexane in a ratio of 1:4 by volume and dried at 50° C. in a vacuum oven for 6 hours. The yield of the di-epoxide of 4,4'-dihydrazondiphenyl sulfone triphenylaminohydrazone was 19.3 g (56%). The product had a melting point of 223–225° C. The $^1$H-NMR spectrum (100 MHz) of di-epoxide of 4,4'-dihydrazondiphenyl sulfone triphenylaminohydrazone in CDCl$_3$ was characterized by the following chemical shifts ($\delta$, ppm): 8.0–6.8 (m, 38H, CH=N, Ar); 4.5–4.3 (dd, 2H, one proton of NCH$_2$); 4.1–3.8 (dd, 2H, another proton of NCH$_2$); 3.2 (m, 2H, CH); 2.9–2.8 (dd, 2H, one proton of OCH$_2$); 2.7–2.5 (dd, another proton of OCH$_2$). An elemental analysis yielded the following results in weight percent: C 74.71; H 5.33; N 9.45, which compared with calculated values for C$_{38}$H$_{35}$N$_5$O$_2$, in weight percent of: C 74.64; H 5.37; N 9.33.

A mixture of di-epoxide of 4,4'-dihydrazondiphenyl sulfone triphenylaminohydrazone (1 g, 1.1 mmol, prepared in the previous step), 4,4'-thiobisbenzenethiol (0.275 g, 1.1 mmol, obtained from Aldrich) and 15 ml of tetrahydrofuran (THF) was added to a 50 ml 3-neck round bottom flask equipped with a reflux condenser and a mechanical stirrer. Then, triethylamine (0.14 ml, 1.1 mmol, from Aldrich, Milwaukee, Wis.) was added to the mixture. The mixture was refluxed under argon for 60 hours. The reaction mixture was cooled to room temperature and filtered through a 3–4 cm layer of silica gel (grade 62, 60–200 mesh, 150 Å). The silica gel was washed with THF. The solution was concentrated to 15–20 ml by evaporation and then poured into a 20-fold excess of methanol with intensive stirring. The resulted precipitate was filtered off and washed repeatedly with methanol and dried under a vacuum at 50° C. The yield of Composition (1) was 1.08 g (84.7%).

Composition (2)

Composition (2) may be prepared according to the procedure for Composition (1) except that 9-ethyl-3-carbazole-carboxaldehyde (0.09 mol) replaces 4-(diphenylamino)benzaldehyde (0.09 mol).

Composition (3)

Composition (3) was prepared according to the procedure for Composition (1) except that 2,5-dimercapto-1,3,4-thiadiazole (0.165 g, 1.1 mmol) replaced thiobisbenzenethiol (0.275 g, 1.1 mmol). The yield of Composition (3) was 1.01 g (86.6%).

Composition (4)

Composition (4) may be prepared according to the procedure for Composition (2) except that 2,5-dimercapto-1,3,4-thiadiazole (0.165 g, 1.1 mmol) replaces thiobisbenzenethiol (0.275 g, 1.1 mmol).

Example 2

Charge Mobility Measurements

This example describes the measurement of charge mobility for samples formed with Compositions (1) and (3) described in Example 1.

Sample 1

A mixture of 0.1 g of the Composition (1) was dissolved in 2 ml of THF. The solution was coated on the methyl cellulose coated polyester film with conductive Al layer by the dip roller method. After drying for 1 h at 80° C., a clear 7 μm thick layer was formed. The hole mobility of the sample was measured and the results are presented in Table 1.

Sample 2

Sample 2 was prepared and tested similarly as Sample 1, except Composition (1) was replaced with Composition (3) and the thickness of the coating was 4 μm.

Mobility Measurements

Each sample was corona charged positively up to a surface potential U and illuminated with 2 ns long nitrogen laser light pulse. The hole mobility μ was determined as described in Kalade et al., "Investigation of charge carrier transfer in electrophotographic layers of chalkogenide glasses," Proceeding IPCS 1994: The Physics and Chemistry of Imaging Systems, Rochester, N.Y., pp. 747–752, incorporated herein by reference. The hole mobility measurement was repeated with changes to the charging regime to charge the sample to different U values, which corresponded to different electric field strength inside the layer E. This dependence on electric field strength was approximated by the formula $$\mu=\mu_0 e^{\alpha\sqrt{E}}.$$

Here E is electric field strength, $\mu_0$ is the zero field mobility and $\alpha$ is Pool-Frenkel parameter. The mobility characterizing parameters $\mu_0$ and $\alpha$ values as well as the mobility value at the 6.4×10$^5$ V/cm field strength as determined from these measurements are given in Table 1.

TABLE 1

| Example | $\mu_0$ (cm$^2$/V · s) | μ (cm$^2$/V · s) at 6.4 · 10$^5$ V/cm | $\alpha$ (cm/V)$^{0.5}$ | Ionization Potential (eV) |
|---|---|---|---|---|
| Sample 1/ Composition (1) | 8 · 10$^{-9}$ | 2 · 10$^{-5}$ | 0.0098 | 5.49 |
| Sample 2/ Composition (3) | ~1 · 10$^{-8}$ | ~6 · 10$^{-5}$ | ~0.011 | 5.49 |

Example 3

Ionization Potential Measurements

This example describes the measurement of the ionization potential for the 2 polymeric charge transport materials described in Example 1.

To perform the ionization potential measurements, a thin layer of polymeric charge transport material about 0.5 μm thickness was coated from a solution of 2 mg of polymeric charge transport material in 0.2 ml of tetrahydrofuran on a 20 cm² substrate surface. The substrate was polyester film with an aluminum layer over a methylcellulose sublayer of about 0.4 µm thickness.

Ionization potential was measured as described in Grigalevicius et al., "3,6-Di(N-diphenylamino)-9-phenylcarbazole and its methyl-substituted derivative as novel hole-transporting amorphous molecular materials," Synthetic Metals 128 (2002), p. 127–131, incorporated herein by reference. In particular, each sample was illuminated with monochromatic light from the quartz monochromator with a deuterium lamp source. The power of the incident light beam was $2$–$5 \cdot 10^{-8}$ W. A negative voltage of −300 V was supplied to the sample substrate. A counter-electrode with the 4.5×15 mm² slit for illumination was placed at 8 mm distance from the sample surface. The counter-electrode was connected to the input of a BK2-16 type electrometer, working in the open input regime, for the photocurrent measurement. A $10^{-15}$–$10^{-12}$ amp photocurrent was flowing in the circuit under illumination. The photocurrent, I, was strongly dependent on the incident light photon energy hv. The $I^{0.5}$=f(hv) dependence was plotted. Usually, the dependence of the square root of photocurrent on incident light quanta energy is well described by linear relationship near the threshold (see references "Ionization Potential of Organic Pigment Film by Atmospheric Photoelectron Emission Analysis," *Electrophotography*, 28, Nr. 4, p. 364 (1989) by E. Miyamoto, Y. Yamaguchi, and M. Yokoyama; and "Photoemission in Solids," Topics in Applied Physics, 26, 1–103 (1978) by M. Cordona and L. Ley, both of which are incorporated herein by reference). The linear part of this dependence was extrapolated to the hv axis, and the Ip value was determined as the photon energy at the interception point. The ionization potential measurement has an error of ±0.03 eV. The ionization potential values are given in Table 1.

As understood by those skilled in the art, additional substitution, variation among substituents, and alternative methods of synthesis and use may be practiced within the scope and intent of the present disclosure of the invention. The embodiments above are intended to be illustrative and not limiting. Additional embodiments are within the claims. Although the present invention has been described with reference to particular embodiments, workers skilled in the art will recognize that changes may be made in form and detail without departing from the spirit and scope of the invention.

What is claimed is:

1. An organophotoreceptor comprising an electrically conductive substrate and a photoconductive element on the electrically conductive substrate, the photoconductive element comprising:

(a) a charge transport composition having the formula

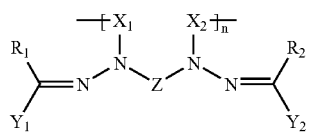

where $Y_1$ and $Y_2$ are, each independently, an arylamine group;

$X_1$ and $X_2$ are, each independently, a linking group;

$R_1$ and $R_2$ are, each independently, a hydrogen, an alkyl group, an alkenyl group, a heterocyclic group, an aromatic group;

Z is a bridging group; and n is a distribution of integers between 1 and 100,000 with an average value greater than 1; and (b) a charge generating compound.

2. An organophotoreceptor according to claim 1 wherein $Y_1$ and $Y_2$, each independently, comprise an (N,N-disubstituted)arylamine group, a julolidine group, or a carbazole group.

3. An organophotoreceptor according to claim 1 wherein $X_1$ and $X_2$ comprise, each independently, a —$(CH_2)_m$— group where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

4. An organophotoreceptor according to claim 3 wherein at least one of the methylene groups is replaced by a heterocyclic group, an aromatic group, a CHOH group, O, or S.

5. An organophotoreceptor according to claim 3 wherein the charge transport composition has the following formula:

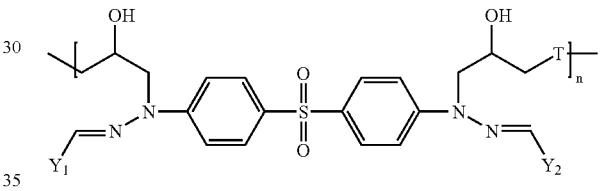

where n is a distribution of integers between 1 and 100,000;

$Y_1$ and $Y_2$ are, each independently, an arylamine group; and

T has one of the following formulae:

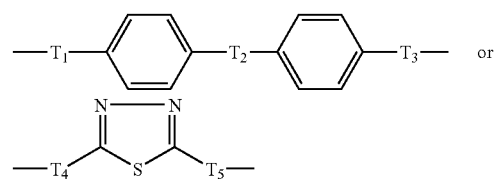

where $T_1$, $T_2$, $T_3$, $T_4$, and $T_5$ are, each independently, O, S, O=S=O, or C=O.

6. An organophotoreceptor according to claim 1 wherein Z comprises a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

7. An organophotoreceptor according to claim 6 wherein Z has the formulae:

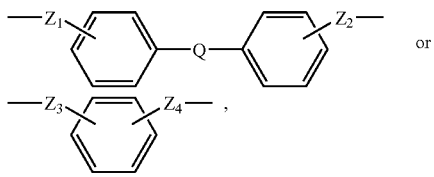

where Q is a bond, O, S, O=S=O, C=O, an aryl group, an $NR_3$ group, or a $CR_4R_5$ group, where $R_3$, $R_4$, and $R_5$ are, each independently, H, an alkyl group, an alkenyl group, a heterocyclic group, an aromatic group, or part of a ring group; and $Z_1$, $Z_2$, $Z_3$, and $Z_4$ are, each independently, a bond or a —$(CH_2)_n$— group where n is an integer between 1 and 20, inclusive, and one or more of the methylene groups is optionally replaced by O, S, N, C, Si, B, P, C=O, O=S=O, a heterocyclic group, an aromatic group, urethane, urea, an ester group, an $NR_6$ group, a $CR_7$ group, a $CR_8R_9$ group, or a $SiR_{10}OR_{11}$ group, where $R_6$, $R_7$, $R_8$, $R_9$, $R_{10}$, and $R_{11}$ are, each independently, a bond, H, hydroxyl, thiol, carboxyl, an amino group, an alkyl group, an alkoxy group, an alkenyl group, a heterocyclic group, an aromatic group, or part of a ring group.

8. An organophotoreceptor according to claim 7 wherein Z has the formula:

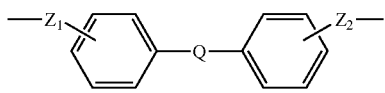

where Q is O=S=O, and $Z_1$ and $Z_2$ are, each independently, a bond.

9. An organophotoreceptor according to claim 1 wherein the photoconductive element further comprises a second charge transport material.

10. An organophotoreceptor according to claim 9 wherein the second charge transport material comprises an electron transport compound.

11. An organophotoreceptor according to claim 1 wherein the photoconductive element further comprises a polymer binder.

12. An electrophotographic imaging apparatus comprising:
(a) a light imaging component; and
(b) an organophotoreceptor oriented to receive light from the light imaging component, the organophotoreceptor comprising an electrically conductive substrate and a photoconductive element on the electrically conductive substrate, the photoconductive element comprising:
(i) a charge transport composition having the formula

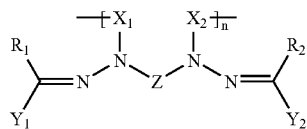

where $Y_1$ and $Y_2$ are, each independently, an arylamine group;

$X_1$ and $X_2$ are, each independently, a linking group;

$R_1$ and $R_2$ are, each independently, a hydrogen, an alkyl group, an alkenyl group, a heterocyclic group, an aromatic group;

Z is a bridging group; and n is a distribution of integers between 1 and 100,000 with an average of greater than 1; and (ii) a charge generating compound.

13. An electrophotographic imaging apparatus according to claim 12 wherein $Y_1$ and $Y_2$, each independently, comprise an (N,N-disubstituted)arylamine group, a julolidine group, or a carbazole group.

14. An electrophotographic imaging apparatus according to claim 12 wherein $X_1$ and $X_2$ comprise, each independently, a —$(CH_2)_m$— group where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

15. An electrophotographic imaging apparatus according to claim 14 wherein at least one of the methylene groups is replaced by a heterocyclic group, an aromatic group, a CHOH group, O, or S.

16. An electrophotographic imaging apparatus according to claim 12 wherein Z comprises a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

17. An electrophotographic imaging apparatus according to claim 16 wherein Z has the formulae:

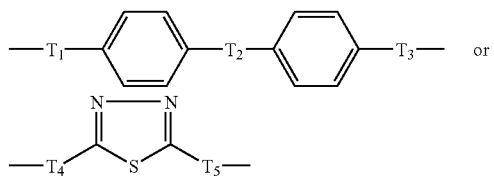

where Q is a bond, O, S, O=S=O, C=O, an aryl group, an $NR_3$ group, or a $CR_4R_5$ group, where $R_3$, $R_4$, and $R_5$ are, each independently, H, an alkyl group, an alkenyl group, a heterocyclic group, an aromatic group, or part of a ring group; and $Z_1$, $Z_2$, $Z_3$, and $Z_4$ are, each independently, a bond or a —$(CH_2)_n$— group where n is an integer between 1 and 20, inclusive, and one or more of the methylene groups is optionally replaced by O, S, N, C, Si, B, P, C=O, O=S=O, a heterocyclic group, an aromatic group, urethane, urea, an ester group, an $NR_6$ group, a $CR_7$ group, a $CR_8R_9$ group, or a $SiR_{10}R_{11}$ group, where $R_6$, $R_7$, $R_8$, $R_9$, $R_{10}$, and $R_{11}$ are, each independently, a bond, H, hydroxyl, thiol, carboxyl, an amino group, an alkyl group, an alkoxy group, an alkenyl group, a heterocyclic group, an aromatic group, or part of a ring group.

18. An electrophotographic imaging apparatus according to claim 17 wherein Z has the formula:

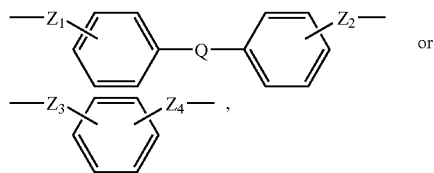

where Q is O=S=O, and $Z_1$ and $Z_2$ are, each independently, a bond.

19. An electrophotographic imaging apparatus according to claim 12 wherein the photoconductive element further comprises an electron transport compound.

20. An electrophotographic imaging apparatus according to claim 12 wherein the photoconductive element further comprises a binder.

21. An electrophotographic imaging apparatus according to claim 12 further comprising a toner dispenser.

22. An electrophotographic imaging process comprising:
(a) applying an electrical charge to a surface of an organophotoreceptor comprising an electrically conductive substrate and a photoconductive element on the electrically conductive substrate, the photoconductive element comprising:
(i) a charge transport composition having the formula

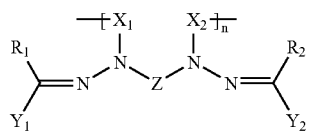

where $Y_1$ and $Y_2$ are, each independently, an arylamine group;
$X_1$ and $X_2$ are, each independently, a linking group;
$R_1$ and $R_2$ are, each independently, a hydrogen, an alkyl group, an alkenyl group, a heterocyclic group, an aromatic group;
Z is a bridging group; and
n is a distribution of integers between 1 and 100,000 with an average greater than 1; and
(ii) a charge generating compound;
(b) imagewise exposing the surface of the organophotoreceptor to radiation to dissipate charge in selected areas and thereby form a pattern of charged and uncharged areas on the surface;
(c) contacting the surface with a toner to create a toned image; and
(d) transferring the toned image to a substrate.

23. An electrophotographic imaging process according to claim 22 wherein $Y_1$ and $Y_2$, each independently, comprise an (N,N-disubstituted)arylamine group, a julolidine group, or a carbazole group.

24. An electrophotographic imaging process according to claim 22 wherein $X_1$ and $X_2$ comprise, each independently, a —$(CH_2)_m$— group where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

25. An electrophotographic imaging process according to claim 22 wherein Z comprises a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

26. An electrophotographic imaging process according to claim 22 wherein the photoconductive element further comprises an electron transport compound.

27. An electrophotographic imaging process according to claim 20 wherein the toner comprises a toner comprising colorant particles.

28. A charge transport composition having the formula:

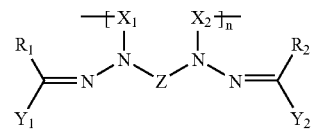

where $Y_1$ and $Y_2$ are, each independently, an arylamine group;
$X_1$ and $X_2$ are, each independently, a linking group;
$R_1$ and $R_2$ are, each independently, a hydrogen, an alkyl group, an alkenyl group, a heterocyclic group, an aromatic group;
Z is a bridging group; and
n is a distribution of integers between 1 and 100,000 with an average greater than 1.

29. A charge transport composition according to claim 28 wherein $Y_1$ and $Y_2$, each independently, comprise an (N,N-disubstituted)arylamine group, a julolidine group, or a carbazole group.

30. A charge transport composition according to claim 28 wherein $X_1$ and $X_2$ comprise, each independently, a —$(CH_2)_m$— group where m is an integer between 1 and 30, inclusive, and one or more of the methylene groups is optionally replaced by O, S, N, C, B, Si, P, C=O, O=S=O, a heterocyclic group, an aromatic group, an $NR_a$ group, a $CR_b$ group, a $CR_cR_d$ group, or a $SiR_eR_f$ where $R_a$, $R_b$, $R_c$, $R_d$, $R_e$, and $R_f$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

31. A charge transport composition according to claim 30 wherein at least one of the methylene groups is replaced by a heterocyclic group, an aromatic group, a CHOH group, O, or S.

32. A charge transport composition according to claim 30 wherein the charge transport composition has the following formula:

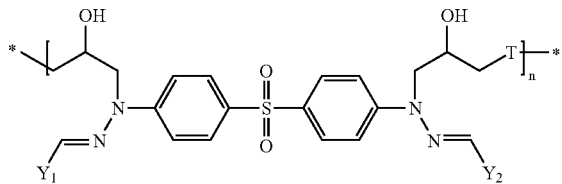

where n is a distribution of integers between 1 and 100,000 with an average value greater than 1;

$Y_1$ and $Y_2$ are, each independently, an arylamine group; and

T has one of the following formulae:

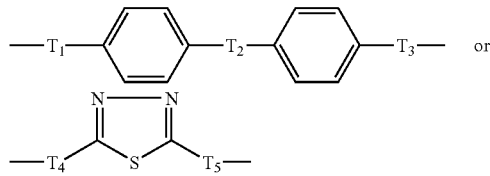

where $T_1$, $T_2$, $T_3$, $T_4$, and $T_5$ are, each independently, O, S, O=S=O, or C=O.

33. A charge transport composition according to claim 28 wherein Z comprises a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group.

34. A charge transport composition according to claim 33 wherein Z has the formulae:

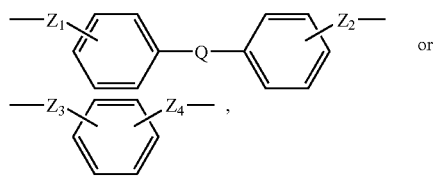

where Q is a bond, O, S, O=S=O, C=O, an aryl group, an $NR_3$ group, or a $CR_4R_5$ group, where $R_3$, $R_4$, and $R_5$ are, each independently, H, an alkyl group, an alkenyl group, a heterocyclic group, an aromatic group, or part of a ring group; and $Z_1$, $Z_2$, $Z_3$, and $Z_4$ are, each independently, a bond or a —$(CH_2)_n$— group where n is an integer between 1 and 20, inclusive, and one or more of the methylene groups is optionally replaced by O, S, N, C, Si, B, P, C=O, O=S=O, a heterocyclic group, an aromatic group, urethane, urea, an ester group, an $NR_6$ group, a $CR_7$ group, a $CR_8R_9$ group, or a $SiR_{10}R_{11}$ group, where $R_6$, $R_7$, $R_8$, $R_9$, $R_{10}$, and $R_{11}$ are, each independently, a bond, H, hydroxyl, thiol, carboxyl, an amino group, an alkyl group, an alkoxy group, an alkenyl group, a heterocyclic group, an aromatic group, or part of a ring group.

35. A charge transport composition according to claim 34 wherein Z has the formulae:

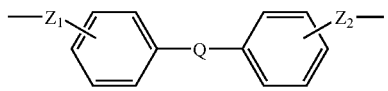

where Q is O=S=O, and $Z_1$ and $Z_2$ are, each independently, a bond.

36. A charge transport composition prepared by co-polymerizing a multi-functional compound comprising at least 2 active hydrogens selected form the group consisting of hydroxyl hydrogen, amino hydrogen, carboxyl hydrogen, and thiol hydrogen with a reactive-ring compound having the following formula

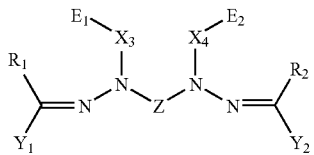

where $Y_1$ and $Y_2$ are, each independently, an arylamine group;

$X_3$ and $X_4$, each independently, comprise a —$(CH_2)_p$— group, where p is an integer between 1 and 20, inclusive, and one or more of the methylene groups is optionally replaced by O, S, N, C, B, Si, P, C=O, O=S=O, a heterocyclic group, an aromatic group, an $NR_m$ group, a $CR_n$ group, a $CR_oR_p$ group, or a $SiR_qR_r$ where $R_m$, $R_n$, $R_o$, $R_p$, $R_q$, and $R_r$ are, each independently, a bond, H, a hydroxyl group, a thiol group, a carboxyl group, an amino group, an alkyl group, an alkoxy group, an alkenyl group, a heterocyclic group, an aromatic group, or part of a ring group;

$R_1$ and $R_2$ are, each independently, a hydrogen, an alkyl group, an alkenyl group, a heterocyclic group, an aromatic group;

Z comprises a —$(CH_2)_k$— group where k is an integer between 1 and 30, inclusive, and one or more of the methylene groups is optionally replaced by O, S, N, C, B, Si, P, C=O, O=S=O, a heterocyclic group, an aromatic group, an $NR_g$ group, a $CR_h$ group, a $CR_iR_j$ group, or a $SiR_kR_l$ where $R_g$, $R_h$, $R_i$, $R_j$, $R_k$, and $R_l$ are, each independently, a bond, H, a hydroxyl group, a thiol group, a carboxyl group, an amino group, an alkyl group, an alkoxy group, an alkenyl group, a heterocyclic group, an aromatic group, or part of a ring group; and $E_1$ and $E_2$ are, each independently, a reactive ring group.

37. A charge transport composition according to claim 36 wherein $E_1$ and $E_2$, each independently, are selected from the group consisting of 3-, 4-, 5-, 7-, 8-, 9-, 10-, 11-, and 12-membered heterocyclic ring groups.

38. A charge transport composition according to claim 36 wherein $E_1$ and $E_2$, each independently, are selected from the group consisting of 3-, 4-, 5-, 7-, 8-, 9-, 10-, 11-, and 12-membered cyclic ethers, cyclic amines, cyclic sulfides, cyclic amides, N-carboxy-a-amino acid anhydrides, lactones, and cyclosiloxanes.

39. A charge transport composition according to claim 36 wherein $E_1$ and $E_2$, each independently, are selected from the group consisting of epoxides, oxetanes, aziridines, thiiranes, 2-azetidinone, 2-pyrrolidone, 2-piperidone, caprolactam, enantholactam, and capryllactam.

40. A charge transport composition according to claim 36 wherein the multi-functional compound is selected from the group consisting of triols, triamines, trithiols, diols, dithiols, diamines, dicarboxlyic acids, hydroxylamines, amino acids, hydroxyl acids, thiol acids, hydroxythiosl, and thioamines.

* * * * *

UNITED STATES PATENT AND TRADEMARK OFFICE
CERTIFICATE OF CORRECTION

PATENT NO. : 7,108,948 B2 Page 1 of 1
APPLICATION NO. : 10/789077
DATED : September 19, 2006
INVENTOR(S) : Zbigniew Tokarski et al.

It is certified that error appears in the above-identified patent and that said Letters Patent is hereby corrected as shown below:

Title page, item (73) should read
Assignee: Samsung Electronics Co., LTD
Kyungki-Do ([[CN]]) KR Signed and Sealed this Sixth Day of November, 2007

JON W. DUDAS
*Director of the United States Patent and Trademark Office*